(12) United States Patent
Narimatsu et al.

(10) Patent No.: US 7,396,666 B2
(45) Date of Patent: Jul. 8, 2008

(54) GLYCOSYLTRANSFERASE, NUCLEIC ACID ENCODING THE GLYCOSYLTRANSFERASE AND METHOD OF TESTING CANCERATION USING THE NUCLEIC ACID

(75) Inventors: Hisashi Narimatsu, Tsukuba (JP); Takashi Kudo, Tsukuba (JP); Akira Togayachi, Tsukuba (JP); Toru Hiruma, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/539,834

(22) PCT Filed: Dec. 26, 2003

(86) PCT No.: PCT/JP03/17030

§ 371 (c)(1),
(2), (4) Date: Jan. 30, 2006

(87) PCT Pub. No.: WO2004/061109

PCT Pub. Date: Jul. 22, 2004

(65) Prior Publication Data

US 2006/0177822 A1      Aug. 10, 2006

(30) Foreign Application Priority Data

Dec. 27, 2002   (JP) .................. 2002-380975

(51) Int. Cl.
C12N 9/10      (2006.01)
C12N 15/00     (2006.01)
C12P 21/06     (2006.01)
C12P 33/20     (2006.01)
C12Q 1/68      (2006.01)
C07H 21/04     (2006.01)
C07K 1/00      (2006.01)

(52) U.S. Cl. ................ 435/97; 435/6; 435/53; 435/69.1; 435/320.1; 435/193; 536/23.2; 536/23.5; 530/350

(58) Field of Classification Search .......... 435/193, 435/6, 69.1, 320.1, 325; 530/350; 536/23.5
See application file for complete search history.

(56) References Cited

U.S. PATENT DOCUMENTS 6,204,029 B1 * 3/2001 Withers et al. ............ 435/97
6,416,988 B1 * 7/2002 Conklin et al. ........... 435/193

FOREIGN PATENT DOCUMENTS

EP          1595955 A1       11/2005
WO          00/34485          6/2000
WO          WO 02/079449 A2 * 10/2002
WO          WO 2004/066948 A2 *  8/2004

OTHER PUBLICATIONS

Vavasseur et al., Synthesis of O-glycan core 3: Characterization of UDP-GlcNAc: GalNAc-R beta3-N-acetyl-glucosaminyltransferase activity from colonic mucosal tissues and lack of activity in human cancer cell lines. Glycobiology, 1995, vol. 5 (3): 351-357.*

Broun et al., Catalytic plasticity of fatty acid modification enzymes underlying chemical diversity of plant lipids. Science, 1998, vol. 282: 1315-1317.*

Witkowski et al., Conversion of b-ketoacyl synthase to a malonyl decarboxylase by replacemnt of the active-site cysteine with glutamine. Biochemistry, 1999, vol. 38: 11643-11650.*

Seffernick et al., Melamine deaminase and Atrazine chlorohydrolase: 98 percent identical but functionally different. J. Bacteriol.,2001, vol. 183 (8): 2405-2410.*

Kataoka et al. "A novel β1,3-N-acetylglucosaminyltransferase involved in invasion of cancer cells as assayed in vitro" Biochem. Biophys. Res. Comm. 294:843-848 (2002).

Strausberg et al. "Generation and initial analysis of more than 15,000 full-length human and mouse cDNA sequences" Proc. Nat. Acad. Sci. USA 99:16899-16903 (2002).

Supplementary Search Report for EP 03786376.8 dated Apr. 26, 2006.

Ishida et al. "A novel β1,3-N-acetylglucosaminyltransferase (β3Gn-T8), which synthesizes poly-N-acetyllactosamine, is dramatically upregulated in colon cancer" FEBS Letters 579:71-78 (2005).

Vavasseur et al., Synthesis of O-glycan core 3: characterization of UDP-GlcNAc: GalNAc-R beta 3-N-acetyl-glucosaminyltransferase activity from colonic mucosal tissues and lack of the activity in human cancer cell lines, *Glycobiology*, 1995, vol. 5, No. 3, pp. 351-357.

Vavasseur et al., *Synthesis of O-glycan core 3: characterization of UDP-GlcNAc: GalNAc-R beta 3-N-acetyl-glucosaminyltransferase activity from colonic mucosal tissues and lack of the activity in human cancer cell lines*, Glycobiology, 1995, vol. 5, No. 3, pp. 351-357.

* cited by examiner

*Primary Examiner*—Rebecca E. Prouty
*Assistant Examiner*—Ganapathirama Raghu
(74) *Attorney, Agent, or Firm*—Nixon & Vanderhye P.C.

(57) ABSTRACT

A tumor marker nucleic acid of the present invention is concerned with a nucleic acid hybridizing under stringent conditions to a nucleotide sequence described in SEQ ID NO: 1 or a complementary nucleotide sequence thereof. A method of testing canceration of the present invention is a method comprising diagnosing a biological sample as being cancerous when the transcription level of the nucleic acid in the biological sample significantly exceeds that in a normal biological sample as a control. The present invention also relates to a β1,3-N-acetyl-D-glucosaminyltransferase protein having an activity of transferring N-acetyl-D-glucosamine from a donor substrate to an acceptor substrate through β1,3-linkage.

6 Claims, 4 Drawing Sheets

Figure 3

| SUBSTRATE (PA-SUGAR) | UDP-GLUCOSAMINE-TRANSFERRING EFFICIENCY (%) | |
| --- | --- | --- |
| | β3GnT2 | G9 |
| PA-001<br>Galβ1-4GlcNAcβ1-2Manα1⟍<br>                    ⁶Manβ1-4GlcNAcβ1-4GlcNAc-PA<br>Galβ1-4GlcNAcβ1-2Manα1⟋³ | 100 | ND |
| PA-002<br>Galβ1-4GlcNAcβ1-2Manα1⟍<br>Galβ1-4GlcNAcβ1⟍     ⁶Manβ1-4GlcNAcβ1-4GlcNAc-PA<br>             ⁴Manα1⟋³<br>Galβ1-4GlcNAcβ1⟋² | 100 | ND |
| PA-004<br>Galβ1-4GlcNAcβ1⟍<br>          ⁶Manα1⟍<br>Galβ1-4GlcNAcβ1⟋²   ⁶Manβ1-4GlcNAcβ1-4GlcNAc-PA<br>Galβ1-4GlcNAcβ1⟍   ³<br>          ⁴Manα1⟋<br>Galβ1-4GlcNAcβ1⟋² | 100 | 14.7 |
| PA-009<br>Galβ1-4GlcNAcβ1-2Manα1⟍    Fucα1⟍<br>                    ⁶Manβ1-4GlcNAcβ1-4GlcNAc-PA<br>Galβ1-4GlcNAcβ1-2Manα1⟋³ | 100 | ND |
| PA-010<br>Galβ1-4GlcNAcβ1-2Manα1⟍    Fucα1⟍<br>Galβ1-4GlcNAcβ1⟍     ⁶Manβ1-4GlcNAcβ1-4GlcNAc-PA<br>             ⁴Manα1⟋³<br>Galβ1-4GlcNAcβ1⟋² | 100 | ND |
| PA-011<br>Galβ1-4GlcNAcβ1⟍<br>          ⁶Manα1⟍    Fucα1⟍<br>Galβ1-4GlcNAcβ1⟋²   ⁶Manβ1-4GlcNAcβ1-4GlcNAc-PA<br>Galβ1-4GlcNAcβ1⟍   ³<br>          ⁴Manα1⟋<br>Galβ1-4GlcNAcβ1⟋² | 100 | 8.9 |
| PA-016<br>Manα1⟍<br>     ⁶Manβ1-4GlcNAcβ1-4GlcNAc-PA<br>Manα1⟋³ | ND | ND |

GLYCOSYLTRANSFERASE, NUCLEIC ACID ENCODING THE GLYCOSYLTRANSFERASE AND METHOD OF TESTING CANCERATION USING THE NUCLEIC ACID

This is a national-phase application of Int'l Appln. No. PCT/JP03/17030 under 35 U.S.C. 371, filed Dec. 26, 2003; the entire content of which is hereby incorporated by reference in this application.

TECHNICAL FIELD

The present invention relates to a novel nucleic acid, the nucleic acid for testing canceration, and a method of testing the canceration of a biological sample based on a difference in the expression level of the nucleic acid in the biological sample; as well as, to a novel glycosyltransferase and a nucleic acid encoding the glycosyltransferase, and the like.

BACKGROUND ART

In recent years, attention has been given to the function of oligosaccharides and glycoconjugates in living bodies. For example, a determinant factor of a blood type is a glycoprotein, and one involved in the function of the nervous system is a glycolipid. Thus, an enzyme having the function of synthesizing an oligosaccharide is a crucially important key for analyzing physiological activities produced by various oligosaccharides.

A N-acetyl-D-glucosamine residue (GlcNAc) and a D-galactose residue (Gal), and the like, in sugar are the components of glycosaminoglycan, while they are sugar residues present in various oligosaccharide structures such as sphingoglycolipids, mucin-type oligosaccharides, and asparagine-linked oligosaccharides (N-linked oligosaccharides). Thus, an enzyme transferring GlcNAc or Gal is a crucially important tool for analyzing the function of oligosaccharides that work in various tissues in living bodies.

For example, at least 20 types of N-acetylglucosaminyltransferases having an activity of transferring GlcNAc have been known as shown in Table 1, each of which differs in acceptor substrate specificity (References 1 to 18).

On the other hand, oligosaccharide synthesis is known to be altered with great frequency in canceration and to be correlated with the metastasis and malignancy of cancer (References 30 to 32). Their comprehensive studies actively conducted today, for example, analysis such as expression profiling in a variety of tissues, are also directed to the elucidation of a canceration mechanism, and discussions have often been conducted on the possibility that the canceration mechanism is associated with the expression level of a particular gene. As well known, the test of tumor markers or the like in blood and the identification of the other gene products involved in canceration, and so on, have already been conducted as methods of cancer diagnostic tests. Tumor markers include many antibodies against oligosaccharides. Among others, immunoassay for oncogene products has often been adopted because of its advantage in high sensitivity.

TABLE 1

N-acetylglucosaminyltransferases and their substrate specificity

| Official name | Abbreviation | Linkage type | Substrate specificty | Reference |
|---|---|---|---|---|
| N-acetylglucosamlnyltransferase-I | GnT-I | β1-2 | Manα1-3(Manα1-6)Manα1-6(Manα1-3)Manβ1-4GlcNAcβ1-4G3cNAcβ1-Asn | 1 |
| N-acetylglucosamlnyltransferase-II | GnT-II | β1-2 | Manα1-6(GlcNacβ1-2Manα1-3)Manβ1-4GlcNAcβ1-Asn | 2 |
| N-acetylglucosamlnyltransferase-III | GnT-III | β1-4 | GlcNAcβ1-2Manα1-6(GlcNAcβ1-2Manα1-3)Manβ1-4GlcNAcβ1-4G3cNAcβ1-Asn | 3 |
| N-acetylglucosamlnyltransferase-IV | GnT-IV | β1-4 | GlcNAcβ1-2(GlcNAcβ1-6)Manα1-6(GlcNAcβ1-2Manα1-3)Manβ1-4GlcNAcβ1-4G3cNAcβ1-Asn | 4 |
| N-acetylglucosamlnyltransferase-V | GnT-V | β1-6 | GlcNAcβ1-2Manα1-6(GlcNAcβ1-2(GlcNAcβ1-4)Manα1-3)Manβ1-4GlcNAcβ1-4G3cNAcβ1-Asn | 5 |
| N-acetylglucosamlnyltransferase-VI | GnT-VI | β1-4 | GlcNAcβ1-2(GlcNAcβ1-6)Manα1-6(GlcNAcβ1-2)(GlcNAcβ1-4)Manα1-3)Manβ1-4GlcNAcβ1-4G3cNAcβ1-Asn | 6 |
| β1,3-N-acetylglucosamlnyltransferase | IGnT | β1-3 | Galβ1-4GlcNAcβ1-R | 7 |
| β1,3-N-acetylglucosamlnyltransferase-2 | β3GnT2 | β1-3 | Galβ1-4GlcNAcβ1-R | 8 |
| β1,3-N-acetylglucosamlnyltransferase-3 | β3GnT3 | β1-3 | Galβ1-3GalNAc-O-S/T | 8 |
| β1,3-N-acetylglucosamlnyltransferase-4 | β3GnT4 | β1-3 | Galβ1-4(GlcNAcβ1-3Gal β1-4) n-R | 8 |
| β1,3-N-acetylglucosamlnyltransferase-5 | β3GnT5 | β1-3 | Galβ1-4GlcNAcβ1-3Gal β1-4-Cer | 9 |
| β1,3-N-acetylglucosamlnyltransferase-6 | β3GnT6 | β1-3 | GalNAc-O-S/T | 10 |
| β1,3-N-acetylglucosamlnyltransferase-7 | β3GnT7 | β1-3 | Galβ1-4(GlcNAcβ1-3Gal β1-4-Cer | 11 |
| β1,3-N-acetylglucosamlnyltransferase | Fringe | β1-3 | C2-X-X-G-G-(Fuc-O) S/T-C3 | 12 |
| β1,6-N-acetylglucosamlnyltransferase | IGnT | β1-6 | GlcNAcβ1-3Galβ1-4GlcNAcβ1-R | 13 |
| Core 2 β1,6-N-acetylglucosamlnyl-transferase-I | C2GnT-I | β1-6 | Galβ1-3GalNAc-O-S/T | 14 |
| Core 2 β1,6-N-acetylglucosamlnyl-transferase-II | C2GnT-II | β1-6 | Galβ1-3GalNAc-O-S/T | 15 |
| Core 2 β1,8-N-acetylglucosamlnyl-transferase-III | C2GnT-III | β1-6 | Galβ1-3GalNAc-O-S/T | 16 |
| α 1,4-N-acetylglucosmlnyltransferase | α 4GnT | α 1-4 | Galβ1-3(Galβ1-4GlcNAcβ1-6)GalNAc-R | 17 |
| peptide β-N-acetylglucosamlnyl-transferase | OGT | O- | Y-S-D-S-P-S-T-S-T | 18 |

Transferring N-acetylglucosamine to an underlined sugar or amino acid.

TABLE 2

References

| 1 | J Biol Chem. 10: 250 (9): 3303-9 (1975) |
| 2 | Can J Biochem Cell Biol. 61 (9): 1049-66. (1983) |
| 3 | J Biol Chem. 10: 257 (17): 10235-42. (1982) |

TABLE 2-continued

References

| | |
|---|---|
| 4 | J Biol Chem. 25: 258 (10): 6162-73. (1983) |
| 5 | J Biol Chem. 25: 257 (22): 13421-7. (1982) |
| 6 | J Biol Chem. 20: 275 (42): 32598-602. (2000) |
| 7 | Cell 105: 957-69 (2001) |
| 8 | J. Biol. Chem. 276 (5). 3498-507 (2001) |
| 9 | J Biol Chem. 276: 22032-40. (2001) |
| 10 | J Biol Chem. 12: 277 (15): 12802-9. (2002) |
| 11 | Biochem. Biophys. Res. Commun. 294 (4). 843-8 (2002) |
| 12 | Nature 406: 411-5 (2000) |
| 13 | J. Biol. Chem. 259: 13385-90 (1984) |
| 14 | J. Biol. Chem. 255: 11253-61 (1980) |
| 15 | J. Biol. Chem. 274: 3215-21 (1999) |
| 16 | J. Biol. Chem. 275: 11106-13 (2000) |
| 17 | Proc. Natl. Acad. Sci. U.S.A. 96, 8991-6 (1999) |
| 18 | J. Biol. Chem. 265: 2563-2568 (1990) |

References

Reference 30: Kobata A., Eur. J. Biochem. 15, 209(2), 483-501, 1992

Reference 31: Santer U. V. et al., Cancer Res., September 44(9), 3730-5, 1984

Reference 32: Taniguchi N., Biochem. Biophys. Acta., 1455 (2-3), 287-300, 1999

As described above, the identification of gene products having some involvement in canceration is expected to provide tumor markers useful in cancer diagnosis. If especially a nucleic acid found in a transcript can be used as an indicator for testing canceration, only the identification of a transcript of a particular gene can sufficiently provide an indicator useful in testing canceration, without the need for elucidating the function of its end product, for example, a protein. Especially the identification of a nucleic acid has advantages which are not found in immunoassay, because it can be performed on a DNA microarray and a nucleic acid even in small amounts can also be quantified after being amplified by PCR.

On the other hand, the function of oligosaccharides in living bodies receives attention. However, the analysis of oligosaccharide synthesis in living bodies does not necessarily progress satisfactorily. This is partly because the mechanism of oligosaccharide synthesis and the localization of sugar synthesis in living bodies are not sufficiently elucidated. The analysis of the mechanism of oligosaccharide synthesis requires the analysis of enzymes synthesizing oligosaccharides, especially glycosyltransferases, and analyzing which type of oligosaccharide is generated with the enzyme. Therefore, there also has been a growing demand for finding a novel glycosyltransferase and analyzing its function.

DISCLOSURE OF THE INVENTION

In light of the above-described problems, an object of the present invention is to provide a tumor marker nucleic acid significantly altered in its transcription level following canceration, a nucleic acid for testing canceration that targets the tumor marker nucleic acid, and a method of testing canceration using any of these nucleic acids.

Another object of the present invention is to provide a nucleic acid encoding a novel human glycosyltransferase protein, and the novel glycosyltransferase protein in the analysis of a particular gene that receives attention as an indicator of the canceration. The glycosyltransferase protein of the present invention is especially a β1,3-N-acetyl-D-glucosaminyltransferase protein having an activity of transferring N-acetyl-D-glucosamine to an acceptor substrate through β1,3-linkage.

A further alternative object of the present invention is to provide a transformant expressing the nucleic acid in a host cell as well as a method of growing the transformant to isolate the protein.

BRIEF DESCRIPTION OF THE DRAWINGS

In FIG. 2A, the effect of pH on the activity was assayed with cacodylate (filled square) and HEPES (N-[2-hydroxyethyl]piperazine-N'-[2-ethanesulfonic acid]) (filled circle) buffers. In FIG. 2B, the effect of a divalent cation was assayed with varying concentrations of $MnCl_2$ (filled circle), $CaCl_2$ (filled square), $MgCl_2$ (filled triangle), $ZnCl_2$ (open circle), $NiSO_4$ (open square), and $CdSO_4$ (open triangle).

FIG. 3 shows the result of activity measurement when oligosaccharides pyridylaminated with 2-aminopyridine (N-glycans) are used as acceptor substrates. ND represents "not detected".

DETAILED DESCRIPTION OF THE INVENTION

Figure 1:
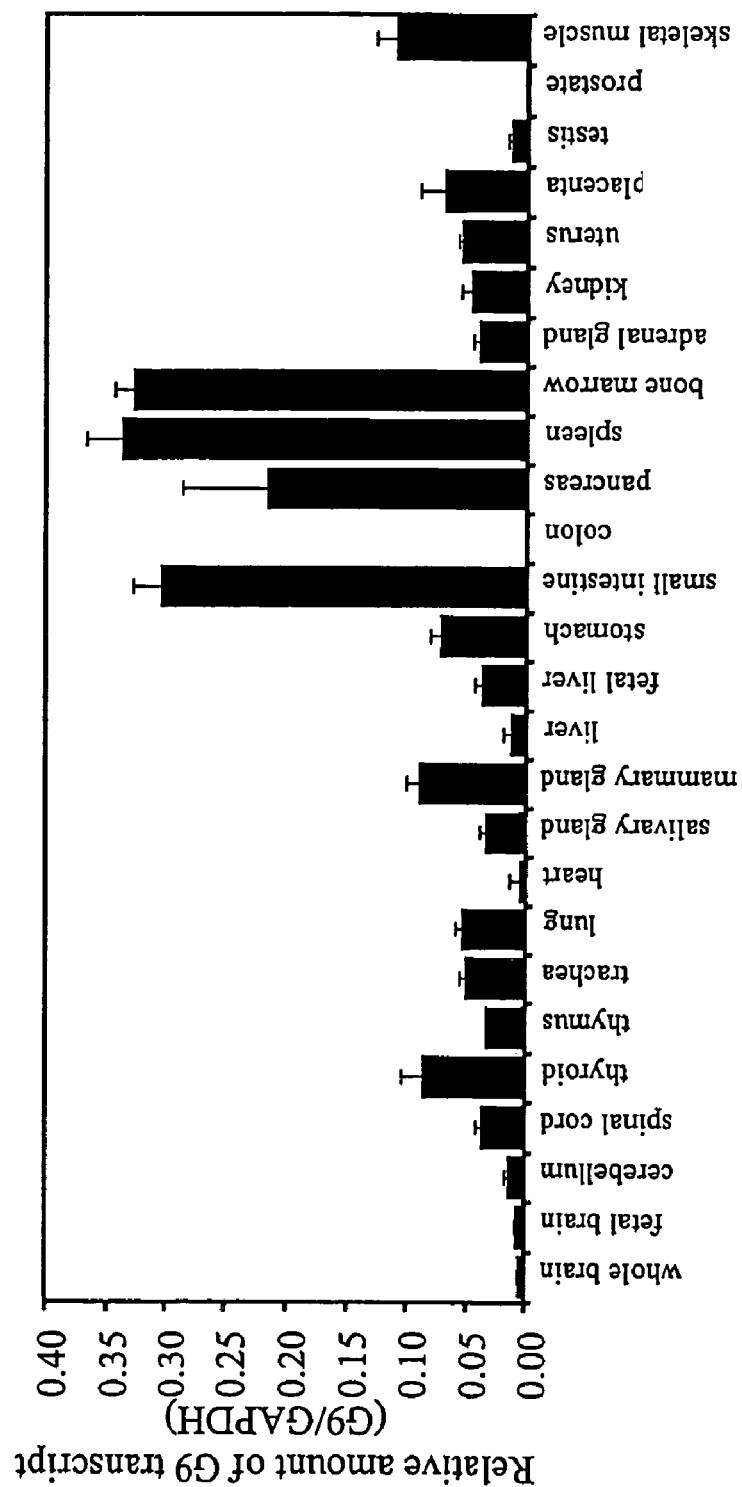
FIG. 1 shows the result of quantitative real-time PCR analysis of G9 transcripts in various human tissues. Calibration curves for G9 and GAPDH (glyceraldehyde-3-phosphate dehydrogenase) were obtained by the serial dilution of the respective plasmid DNAs. The expression level of the G9 transcript was adjusted to the GAPDH measured for equivalent cDNA. The data was shown as the average ±S.D. of values obtained from three experiments.

The present inventors attempted the isolation and purification of a nucleic acid of interest that seems to have high sequence homology based on the nucleotide sequence of a gene of an enzyme similar in action to an enzyme of interest. Specifically, at first, the present inventors conducted a BLAST search using the sequence of a β1,3-N-acetylglucosaminyltransferase, a glycosyltransferase known in the art, as a query sequence and consequently found a genome sequence (GenBank No. AC011462) as a sequence having homology.

Further, the present inventors successfully cloned a gene encoding the protein by PCR and determined its nucleotide sequence (SEQ ID NO: 1) and predicted amino acid sequence (SEQ ID NO.: 2). A gene having the nucleotide sequence of SEQ ID NO: 1 was designated as a G9 gene, and a protein having the amino acid sequence of SEQ ID NO: 2 was designated as a G9 protein. The present inventors have thereby completed the present invention by finding out that a protein encoded by the nucleic acid is a novel glycosyltransferase and that the presence or absence of the expression of the nucleic acid or its expression level in cancerous tissues differs from that in normal tissues. The present inventors further allowed the expression of the nucleic acid obtained in the present invention by a genetic engineering technique to yield a recombinant protein. The investigation of the activity of a protein of the present invention has revealed that the protein is a β1,3-N-acetyl-D-glucosaminyltransferase protein having an activity of transferring N-acetyl-D-glucosamine from a donor substrate to an acceptor substrate through β1,3-linkage.

The present invention relates to a nucleic acid hybridizing under stringent conditions to a nucleotide sequence described in SEQ ID NO: 1 or a complementary nucleotide sequence thereof.

Preferably, the nucleic acid of the present invention consists of a nucleotide sequence having at least 15 contiguous nucleotides in a nucleotide sequence described in SEQ ID NO: 1 or a complementary nucleotide sequence thereof.

The nucleic acid of the present invention is typically a probe or a primer. The nucleic acid of the present invention can also be a tumor marker.

The present invention also relates to a method of testing the canceration of a biological sample, comprising:

(a) using any of the above-described nucleic acids to measure the transcription level of the nucleic acid in a biological sample; and (b) diagnosing the biological sample as being cancerous when the transcription level of the nucleic acid in the biological sample significantly exceeds that in a normal biological sample as a control.

According to a preferred aspect of the testing method by the present invention, the method of testing the canceration of a biological sample comprises:

(a) using any of the above-described nucleic acids as a labeled probe, which is in turn brought into contact with a biological sample under stringent hybridization conditions to measure the transcription level of the nucleic acid in the biological sample based on a signal from the label of the hybridized nucleic acid; and (b) diagnosing the biological sample as being cancerous when the transcription level of the nucleic acid in the biological sample significantly exceeds that in a normal biological sample as a control.

According to another preferred aspect of the testing method by the present invention, the method of testing the canceration of a biological sample comprises:

(a) using the above-described primer that is labeled to subject a biological sample to nucleic acid amplification and measuring the amount of a resulting nucleic acid amplification product; and (b) diagnosing the biological sample as being cancerous when the amount of the nucleic acid amplification product significantly exceeds that in a normal biological sample as a control.

According to a further aspect of the testing method by the present invention, the effectiveness of treatment for cancer therapy can be examined by use of the nucleic acid of the present invention.

The method of examining the effectiveness of treatment for cancer therapy by the present invention is a method comprising:

using any of the nucleic acids according to the present invention to measure the transcription level of the nucleic acid in a biological sample that has received treatment for cancer therapy and comparing its measurement value with that before the treatment or without the treatment, thereby determining whether the treatment given to the biological sample is effective or not.

A preferred aspect of the method of examining the effectiveness of treatment by the present invention encompasses a method comprising: using the biological sample which has already been cancerous, and determining that treatment for cancer therapy given to the biological sample is effective if the transcription level of the nucleic acid in the biological sample that has received the treatment is significantly below that before the treatment or without the treatment.

The biological sample to which the method of examining the effectiveness of treatment can be applied includes an in vivo biological sample from a non-human model animal as well as an in vitro biological sample derived from a tissue, a cell, or the like (including a human tissue or cell, or the like). Alternatively the biological sample to which each of the above-described methods according to the present invention can be applied is typically a sample derived from the large intestine or peripheral blood.

In other aspects of the present invention, the nucleotide sequence of SEQ ID NO: 1 has 31% homology to those of known genes a human β1,3GlcNAc transferase 2 and a β1,3Gal transferase 6, and a conserved motif therein is close to that in a β1,3Gal transferase. The nucleotide sequence has 60% homology to that of a murine β1,3GlcNAc transferase 1. The predicted amino acid sequence of SEQ ID NO: 2 has a hydrophobic transmembrane region characteristic of a glycosyltransferase at its N terminus.

From these points of view, the nucleic acid sequence of SEQ ID NO: 1 presumably encodes a novel human glycosyltransferase that transfers an N-acetyl-D-glucosamine residue to synthesize an oligosaccharide through β1,3-linkage. In actuality, an enzyme protein having a biological activity was isolated and purified therefrom and a certain activity was confirmed (Examples 4 and 5).

Since a protein consisting of the amino acid sequence of SEQ ID NO: 2 has the activity of the novel glycosyltransferase, providing an amino acid sequence of this novel protein and a nucleic acid encoding it would make a contribution toward satisfying diverse needs for them in the art.

That is, the present invention also relates to a glycosyltransferase protein that transfers an N-acetyl-D-glucosamine residue from a sugar donor substrate to a sugar acceptor substrate through β1,3-linkage and relates to a nucleic acid encoding the protein. The typical sugar donor substrate is UDP-GlcNac, and at least a Galβ1,4GlcNAc carbohydrate residue is the acceptor substrate.

Thus, the present invention also relates to a β1,3-N-acetyl-D-glucosamintyltransferase protein having an activity of transferring N-acetyl-D-glucosamine from donor substrate to an acceptor substrate through β1,3-linkage, wherein "β" represents an anomer having a cis configuration, of anomers of glycosidic linkage at position 1 of the sugar ring.

Moreover, the glycosyltransferase protein of the present invention includes a glycosyltransferase protein that has at least one of the following properties (a) to (c):

(a) acceptor substrate specificity:

the glycosyltransferase protein has a significant transferring activity for at least Bz-β-lactoside and/or Galβ1-4GlcNAc groups, wherein "Bz" represents a benzyl group, "Gal" represents a galactose residue, "GlcNAc" represents an N-acetyl-D-glucosamine residue, and "β" represents an anomer having a cis configuration, of anomers of glycosidic linkage at position 1 of the sugar ring;

(b) reaction pH:

the glycosyltransferase protein has a-high activity at or around neutral; or (c) divalent ion requirement:

the activity is enhanced in the presence of at least $Mn^{2+}$ or $CO^{2+}$.

The glycosyltransferase protein of the present invention particularly includes a glycosyltransferase protein that has a significant activity for an acceptor substrate having an N-linked oligosaccharide with four Galβ1-4GlcNAc groups.

In addition, an aspect of the glycosyltransferase protein of the present invention includes a glycosyltransferase protein that has any one sequence of the following (A) to (C):

(A) any one amino acid sequence of SEQ ID NO: 2, SEQ ID NO: 16, or SEQ ID NO: 17;

(B) an amino acid sequence comprising any one amino acid sequence of SEQ ID NO: 2, SEQ ID NO: 16, or SEQ ID NO: 17 in which one or several amino acid(s) is(are) substituted, deleted, or inserted; or (C) an amino acid sequence having at least 40% identity to any one amino acid sequence of SEQ ID NO: 2, SEQ ID NO: 16, or SEQ ID NO: 17.

In an alternative aspect, the present invention also relates to a nucleic acid encoding a β1,3-N-acetyl-D-glucosaminyltransferase protein according to any of the above-described aspects.

An aspect of the nucleic acid encoding a glycosyltransferase protein of the present invention encompasses a nucleic acid that comprises a full-length nucleotide sequence described in SEQ ID NO: 1, nucleotide sequence from nucleotide Nos. 76 to 1194 therein, a nucleotide sequence from nucleotide Nos. 97 to 1194 therein, or any of complementary nucleotide sequences thereof. Such a nucleic acid can be DNA.

In a further alternative aspect, the present invention also relates to a vector comprising a nucleic acid encoding a glycosyltransferase protein as described above as well as a transformant comprising the vector. The present invention further relates to a method of producing a β1,3-N-acetyl-D-glucosaminyltransferase protein, comprising: growing the above-described transformant and expressing the glycosyltransferase protein to collect the glycosyltransferase protein from the transformant.

In a still alternative aspect, the present invention can provide an antibody recognizing a β1,3-N-acetyl-D-glucosaminyltransferase protein according to any of the above-described aspects.

The finding that the nucleic acid of the present invention encodes a novel glycosyltransferase protein suggests that the expression level of the glycosyltransferase protein in a cancer tissue exceeds that in a normal tissue. Accordingly, it may be possible to test the canceration of a biological sample by detecting or quantifying the protein of the present invention that is expressed in the biological sample to compare its result with that of a normal biological sample as a control.

Thus, the present invention also relates to a method of testing the canceration of a biological sample, comprising the steps of:

(a) detecting or quantifying the novel glycosyltransferase protein of the present invention in a biological sample; and (b) diagnosing the biological sample as being cancerous when the quantified value of the glycosyltransferase protein in the biological sample significantly exceeds that of the glycosyltransferase protein in a normal biological sample as a control.

Here, the use of an antibody specifically recognizing a glycosyltransferase protein is exemplified for detecting the novel glycosyltransferase protein.

PREFERRED MODE OF CARRYING OUT THE INVENTION

Hereinafter, the present invention will be described in detail in accordance with embodiments of the present invention.

(1) Nucleic Acid of the Present Invention Involved in Canceration

The present inventors have found that the canceration of a normal tissue, for example, a human large intestine tissue, without the expression of a nucleic acid having a nucleotide sequence described in SEQ ID NO: 1 is confirmed to cause the nucleic acid to be expressed therein, and that a normal tissue, for example, peripheral blood from a patient with colorectal cancer, in which a nucleic acid having a nucleotide sequence described in SEQ ID NO: 1 is generally expressed has a significant increase in the expression level of the nucleic acid as compared to that in a normal individual.

Thus, a nucleic acid consisting of the nucleotide sequence of SEQ ID NO: 1 or a complementary sequence thereof is worthy of note as a tumor marker useful in examination for a transcript in a biological sample. According to the present invention, a nucleic acid capable of specifically hybridizing under stringent conditions to this tumor marker nucleic acid is provided.

A primer or probe according to the present invention is typically a natural DNA fragment derived from a nucleic acid having a nucleotide sequence of SEQ ID NO: 1, a synthetic DNA fragment designed to have a nucleotide sequence of SEQ ID NO: 1, or any of complementary strands thereof.

Especially the tumor marker nucleic acid was detected via a BLAST search and is transcribed as mRNA encoding a structural gene. In general, its full-length ORF or a portion thereof can be present in a sample. From this point of view, using the nucleic acid as a targeting primer or probe, a desired target sequence can be selected from across the ORF of the nucleotide sequence of SEQ ID NO: 1. The primer or probe of the present invention can be a partial sequence in the nucleotide sequence of SEQ ID NO: 1.

Using the primer or probe as described above, the target nucleic acid in a biological sample can be detected and/or quantified as described below. Because a genomic sequence or the like can be targeted, the nucleic acid of the present invention can also be provided as an antisense primer for medical research or gene therapy.

Probe of the Present Invention

When the nucleic acid of the present invention is used as a probe, the nucleic acid is an oligonucleotide with 15 bases or more, preferably 20 bases or more, selected from the nucleotide sequence of SEQ ID NO: 1 or a complementary strand thereof, or alternatively cDNA with a maximum length of a full-length ORF region (i.e., 1191 bases: nucleotide Nos. 1 to 1191) in the nucleotide sequence of SEQ ID NO: 1 or a complementary strand thereof.

In particular, the probe of the present invention is widely useful as a reagent or a diagnostic agent for medical research. Considering that a nucleic acid having an exceedingly large molecular weight is generally difficult to handle, a preferred base length of the probe is exemplified by 50 to 500 bases, more preferably 60 to 300 bases.

Depending on, for example, the base length or hybridization conditions adopted, an oligonucleotide probe having a relatively short strand can function as a probe even if there is a mismatch on the order of one or several bases, especially one or two bases, between the oligonucleotide probe and the nucleotide sequence of SEQ ID NO: 1 or the complementary nucleotide sequence thereof. A cDNA probe having a relatively long strand can function as a probe even if there is a mismatch of 50% or less, preferably 20% or less, between the cDNA probe and the nucleotide sequence of SEQ ID NO: 1 or the complementary nucleotide sequence thereof.

Alternatively, when the nucleic acid of the present invention is a synthetic oligonucleotide, the number of bases therein is 15 bases or more, preferably 20 bases or more. Depending on the base length or hybridization conditions adopted, the synthetic oligonucleotide can function as a probe even if there is a mismatch on the order of one or several bases, especially one or two bases, between the synthetic oligonucleotide and the nucleotide sequence described in SEQ ID NO: 1 or the complementary nucleotide sequence thereof.

It should be understood that the oligonucleotide probe according to the present invention having 15 bases in length could specifically hybridize under stringent conditions to the target nucleic acid. Those skilled in the art can select a suitable partial sequence with at least 15 bases from the nucleotide sequence of SEQ ID NO: 1 according to various strategies concerning oligonucleotide probe design known in the art. Moreover, information from an amino acid sequence of SEQ ID NO: 2 would be helpful in selecting a unique sequence likely to be suitable as a probe.

"Under stringent conditions" used herein means hybridization under moderately or highly stringent conditions. Specifically, the moderately stringent conditions are based on, for example, the length of DNA and can readily be determined by those having ordinary skill in the art. Basic conditions are shown in Sambrook et al., Molecular Cloning: A Laboratory Manual, 3rd ed., Vol. 1, 7.42-7.45 Cold Spring Harbor Laboratory Press, 2001 and include, for a nitrocellulose filter, the use of hybridization conditions comprising a prewashing solution containing 5×SSC, 0.5% SDS, 1.0 mM EDTA (pH: 8.0) and a hybridization solution containing approximately 50% formamide, 2×SSC to 6×SSC at approximately 40 to 50° C. (or other similar hybridization solutions such as a Stark's solution in approximately 50% formamide at approximately 42° C.), and washing conditions comprising 0.5×SSC, 0.1% SDS at approximately 60° C. The highly stringent conditions are also based on, for example, the length of DNA and can readily be determined by those skilled in the art. In general, such conditions include hybridization and/or washing at a temperature higher than that of the moderately stringent conditions and/or a salt concentration lower than that of the moderately stringent conditions and are defined by involving, for example, the hybridization conditions as described above and washing in 0.2×SSC, 0.1% SDS at approximately 68° C. Those skilled in the art would appreciate that a temperature and a salt concentration of a washing solution is optionally adjustable according to factors such as the length of a probe.

As described above, those skilled in the art can readily find and practice moderately or highly stringent conditions suitable for a selected probe, based on common general technical knowledge in various probe design methods and hybridization conditions known in the art as well as empirical rules that would be obtained through experimental means usually used.

The probe of the present invention includes a labeled probe attached with a label such as fluorescent, radioactive, and biotin labels, in order to detect or confirm the probe hybridized with the target sequence. One example of the labeled probe according to the present invention is an oligonucleotide consisting of a nucleotide sequence of SEQ ID NO: 6 (which corresponds to a complementary strand of a strand from nucleotide Nos. 485 to 502 in SEQ ID NO: 1). This labeled probe can be used for confirming or quantifying a PCR product of the target nucleic acid. The labeled probe of the present invention may also be integrated in a diagnostic DNA probe kit or the like or may be immobilized on a chip such as a DNA microarray.

Primer of the Present Invention

When the nucleic acid of the present invention is used as a primer, the nucleic acid is an oligonucleotide. Specifically, two regions are selected from the ORF region in the nucleotide sequence of SEQ ID NO: 1 to satisfy the following conditions:

1) each of the regions has a length of 15 bases or more, preferably 18 bases or more, more preferably 21 bases or more and no longer than 50 bases; and 2) each of the regions has a G+C content of 40 to 70%. Single-stranded DNAs having the same nucleotide sequences as those of the two selected regions or nucleotide sequences complementary to those of the regions may be produced, or otherwise the single-stranded DNAs modified to maintain the binding specificity for the nucleotide sequences may be produced. Preferably, the primer of the present invention has a sequence completely complementary to a partial sequence in the ORF region of SEQ ID NO: 1 and however, may have a one- or two-base mismatch.

One example of a pair of primers according to the present invention is a pair of an oligonucleotide consisting of a nucleotide sequence described in SEQ ID NO: 4 (which corresponds to a complementary strand of a strand from nucleotide Nos. 450 to 469 in SEQ ID NO: 1) and an oligonucleotide consisting of a nucleotide sequence described in SEQ ID NO: 5 (which corresponds to a complementary strand of a strand from nucleotide Nos. 531 to 549 in SEQ ID NO: 1).

A probe selected from the nucleotide sequence positioned between a pair of primers used can be employed for quantifying the target nucleic acid amplified by PCR. One example of a labeled probe for detecting a PCR product is an oligonucleotide consisting of a nucleotide sequence described in SEQ ID NO: 6 (which corresponds to a complementary strand of a strand from nucleotide Nos. 485 to 502 in SEQ ID NO: 1).

(2) Method of Testing Canceration According to the Present Invention

According to a method of testing canceration of the present invention, the transcription level of the target nucleic acid in a transcript of a biological sample can be measured. Its measurement result is compared with a result from a normal biological sample as a control. If a significant difference lies between those results, the biological sample can be diagnosed as being a cancerous tissue.

In this testing method, a threshold normalized in advance on the basis of known data concerning a normal biological sample may be used as a detection result for a normal tissue used as a control. For example, when a normal tissue is not obtained from an identical patient as in the test of peripheral blood, comparison with the average of values measured in normal individuals is performed.

As used herein, the significant difference to be diagnosed as being cancerous means that the substantial presence (i.e., significant concentration) of the target nucleic acid in a subject tissue is confirmed if the target nucleic acid is expressed in a normal tissue as in, for example, peripheral blood from a patient with colorectal cancer, or that the concentration of the nucleic acid in a subject tissue significantly exceeds that in a normal tissue and preferably the nucleic acid in the subject tissue is not less than 1.5 times, preferably 2 times, by concentration greater than that in the normal tissue when the target nucleic acid is generally expressed in a normal tissue as in, for example, a colorectal cancer tissue.

The method of testing canceration according to the present invention typically involves a hybridization assay and a PCR method.

Hybridization Assay

Examples of a hybridization assay that can be used in the present invention include various hybridization assays well known to those skilled in the art such as a southern blot, northern blot, dot blot, or a colony hybridization technique for a transcript extracted from a biological sample.

Depending on the transcription amount of the target nucleic acid or a difference from a normal tissue, a testing method known in the art including a quantitative hybridization assay such as dot blot or colony hybridization used alone or in combination with immunoassay may be employed when the quantification of the target nucleic acid or an increase in detection level is required.

According to the typical hybridization assay, a subject nucleic acid extracted from a biological sample or an amplification product thereof is immobilized on a solid phase and hybridized under stringent conditions to a labeled probe to measure the label bound to the solid phase after washing.

Every method known to those skilled in the art can be applied to the extraction and purification of a transcript from a biological sample. That purified from a biological sample and subjected to the hybridization assay is typically cDNA from the whole transcript of the biological sample. However, when canceration is determined only by the substantial detection of the target nucleic acid (i.e., when no target nucleic acid appears to be expressed in a normal tissue), the use of a testing method such as in situ hybridization in no need of the purification or the like of a transcript would be practical for a subject tissue in clinical tests.

Testing Method by Nucleic Acid Amplification

On the basis of "the nucleotide sequence of the nucleic acid of the present invention", those skilled in the art can appropriately create primers based on nucleotide sequences positioned at both ends of the nucleic acid of the present invention or a partial region of interest thereof to be prepared, and readily amplify and prepare the region of interest by nucleic acid amplification reaction (e.g., PCR) using the primers.

As used herein, examples of the nucleic acid amplification reaction include reaction requiring thermal cycles such as polymerase chain reaction (PCR) [Saiki R. K., et al., Science, 230, 1350-1354 (1985)], ligase chain reaction (LCR) [Wu D. Y., et al., Genomics, 4, 560-569 (1989); Barringer K. J., et al., Gene, 89, 117-122 (1990); Barany F., Proc. Natl. Acad. Sci. USA, 88, 189-193 (1991)], and transcription-based amplification [Kwoh D. Y., et al., Proc. Natl. Acad. Sci. USA, 86, 1173-1177 (1989)], and isothermal reaction such as strand displacement amplification (SDA) [Walker G. T., et al., Proc. Natl. Acad. Sci. USA, 89, 392-396 (1992); Walker G. T., et al., Nuc. Acids Res., 20, 1691-1696 (1992)], self-sustained sequence replication (3SR) [Guatelli J. C., Proc. Natl. Acad. Sci. USA, 87, 1874-1878 (1990)], and Qβ replicase system [Lizardi et al., BioTechnology 6, p. 1197-1202 (1988)]. For example, Nucleic Acid Sequence-Based Amplification (NASBA) reaction described in European Patent No. 0525882, which employs the competitive amplification of a target nucleic acid with a mutant sequence is also available. Preferably, the nucleic acid amplification reaction is the PCR method.

The target nucleic acid in a transcript can be detected using PCR method with, for example, a pair of primers of the present invention selected from the target nucleic acid. In general, the nucleic acid amplification method in itself, such as PCR, is well known in the art and is readily carried out because a reagent kit and an apparatus for the nucleic acid amplification method are commercially available.

When the primer pair of the present invention is used to carry out a nucleic acid amplification method by PCR with the subject nucleic acid as a template, the subject nucleic acid present in a sample is amplified while no amplification takes place in a sample without the subject nucleic acid. Therefore, whether or not the subject nucleic acid is present in the sample can be determined by confirming the presence of an amplification product, and the transcription level of the subject nucleic acid, that is, the concentration thereof can also be determined by quantifying an amplification product. PCR cycles when repeated a predetermined number of times would amplify the subject nucleic acid to a desired concentration. The nucleic acid in a normal tissue can also be measured in a similar way. A nucleic acid of a gene extensively and generally present in an identical tissue or the like, for example, a nucleic acid encoding glyceraldehyde-3-phosphate dehydrogenase (GAPDH) or β-actin may be used as a control.

The subject nucleic acid may be the whole mRNA as a transcript extracted from a biological sample such as a subject tissue or cell or may be the whole cDNA reverse-transcribed from the mRNA. When mRNA as the subject nucleic acid is amplified, a NASBA method (3SR method, TMA method) using the above-described pair of primers may be adopted. The NASBA method in itself is well known and can readily be practiced using the pair of primers because a kit for the NASBA method is commercially available.

An amplification product obtained by PCR method can be detected or quantified by procedures where the reaction solution after amplification is subjected to electrophoresis and the resulting bands are stained with ethidium bromide or the like or procedures where the amplification product after electrophoresis is immobilized on a solid phase such as a nylon membrane and hybridized to a labeled probe specifically hybridizing to the subject nucleic acid, for example, a labeled probe described in SEQ ID NO: 6, to detect the label after washing.

When the "concentrations" of the target nucleic acids are compared between a subject tissue and a normal tissue, it is preferable to use a quantitative PCR method including a RT-PCR or quantitative real-time PCR method for kinetic analysis. Because the target nucleic acid previously purified is mRNA, a quantitative real-time RT-PCR method is particularly preferred. However, the quantification of the nucleic acid in the present testing method is not limited to the quantitative PCR method, and other DNA quantification methods known in the art such as northern blot, dot blot, and a DNA microarray using the above-described probe for a PCR product are applicable.

It is also possible to quantify the amount of the target nucleic acid in a sample by carrying out quantitative RT-PCR using quencher and reporter fluorescent dyes. Because especially a kit for the quantitative RT-PCR is commercially available, the quantitative RT-PCR can readily be carried out. In addition, it is also possible to semi-quantify the target nucleic acid based on the strength of electrophoretic bands.

Testing Method for Effectiveness of Cancer Therapy

The above-described method of testing canceration according to the present invention can also be employed as a method of examining the effectiveness of cancer therapy. Subjects to be examined are the effectiveness of treatment for which the effectiveness of cancer cure should be examined as well as the effectiveness of treatment given to a cancerous cell or tissue or a tumor tissue or the like obtained from a model animal for experimental carcinogenesis. Such treatment includes every prescription such as radiotherapy in addition to the administration of an anticancer agent. The treatment is given to a cancerous biological sample or to the focus of an experimental model animal.

According to a method of examining the effectiveness of cancer therapy according to the present invention, the transcription level of the target nucleic acid in a biological sample that has received treatment of interest is compared with that before the treatment or without the treatment. Alternatively, the transcription level may also be followed up after the treatment. The treatment can be assessed as being effective for cancer therapy if by using it the treatment causes the transcription level to be significantly reduced or causes an intentional rise in the transcription level to be significantly suppressed.

Such examination includes determination about whether a candidate substance of an anticancer agent given to a cancerous tissue is effective or not, especially whether the candidate substance is effective or not for a lesion tissue or the like in an experimental model animal, and determination about whether a novel candidate anticancer agent is effective or not for a patient with cancer. To the contrary, assessment of whether carcinogenicity is suppressed or not in an experimental model animal designed to develop cancer, that is, whether an expected rise in the transcription level is significantly suppressed or not is also targeted.

In the present specification, the "transcription level" or "transcription amount" of a nucleic acid refers to the abundance of the nucleic acid derived from a transcript in a fixed amount of a biological sample. Because a nucleic acid can be amplified for quantification or the signal level of its label can be amplified, the amount of the nucleic acid measured can also be expressed as an amplified amount or an amplified signal level.

In the present specification, a "subject nucleic acid" or "target nucleic acid" includes not only mRNA and siRNA but also every type-of nucleic acid obtained with mRNA as a template, regardless of in vivo or in vitro origin.

In the present specification, a "biological sample" refers to an organ, a tissue, and a cell as well as an experimental animal-derived organ, tissue, and cell, etc., and is preferably a tissue. The esophagus, the stomach, the pancreas, the liver, the kidney, the duodenum, the small intestine, the large intestine, the rectum, the colon, and peripheral blood are concretely exemplified. Preferred are the large intestine, the rectum, the colon, and peripheral blood, and more preferred are the large intestine and peripheral blood. The term "measurement" used herein encompasses any of detection, amplification, quantification, and semi-quantification. The application of the nucleic acid of the present invention also includes gene therapy.

The testing method of the present invention is a method of testing the canceration of a biological sample as described above. The phrase "testing canceration" used herein includes testing to determine whether the biological sample develops cancer or not as well as testing to determine whether malignancy is high or not, and can be applied to diagnosis, therapy, and so on, for cancer in medical care. The term "cancer" used herein typically refers to the entire spectrum of malignant tumors and includes disease conditions caused by a malignant tumor. The testing method of the present invention is suitable for testing, but not limited to, cancer of the esophagus, gastric cancer, cancer of the pancreas, cancer of the liver, renal cancer, duodenal cancer, cancer of the small intestine, colorectal cancer, cancer of the rectum, cancer of the colon, and peripheral blood. Preferred are colorectal cancer, cancer of the rectum, and cancer of the colon, and more preferred is colorectal cancer.

(3) Nucleic Acid of the Present Invention Encoding Novel Glycosyltransferase

Based on the finding of the nucleic acid described above, the present invention also provides a nucleic acid encoding a full-length novel glycosyltransferase protein or a fragment thereof.

The nucleic acid of the present invention encoding a novel glycosyltransferase is a nucleic acid consisting of a nucleotide sequence described in SEQ ID NO: 1 or a complementary nucleotide sequence thereof, preferably a nucleic acid consisting of a nucleotide sequence from nucleotide Nos. 76 to 1194 in SEQ ID NO: 1. The nucleic acid of SEQ ID NO: 1 includes those encoding an amino acid sequence of SEQ ID NO: 2, and the nucleic acid with the nucleotide sequence from nucleotide Nos. 76 to 1194 in SEQ ID NO: 1 includes nucleic acids encoding amino acid sequences of SEQ ID NOs: 16 and 17. A nucleic acid encoding an amino acid sequence identical to any amino acid sequence encoded by those nucleic acids because of codon degeneracy is also encompassed by the present invention. As previously described, these nucleic acids are nucleic acids suitable for use in, for example, the method of testing canceration.

The nucleic acid of the present invention encoding the novel glycosyltransferase includes both single-stranded and double-stranded DNAs and also includes RNA complements thereof. Examples of the DNA include naturally-derived DNA, recombinant DNA, DNAs chemically bonded together, DNA amplified by PCR, and combinations thereof. However, DNA is preferred in light of its stability at the time of preparing a vector and a transformant.

The nucleic acid of the present invention may be prepared by, for example, procedures below.

At first, a candidate gene likely to encode a homolog protein of a β1,3-N-acetylglucosaminyltransferase, a glycosyltransferase known in the art, is searched, and its amino acid (polypeptide) sequence is determined: when a program such as BLAST is used to search a gene having a homology to a β1,3-N-acetylglucosaminyltransferase gene from a gene database, for example, a human genome DNA sequence (AC011462: Homo sapiens chromosome 19 clone CTC-435M10) and EST (expressed sequence tag, AW444713) sequence likely to encode its homolog protein are found.

A complementary sequence of the nucleic acid found as above or a portion thereof is utilized to carry out nucleic acid amplification reaction from a cDNA library or the like according to a standard method using a basic genetic engineering approach such as hybridization and nucleic acid amplification reaction, thereby allowing the preparation of the nucleic acid of the present invention. Because, for example, an approximately 1.2-kbp DNA fragment is obtained as a PCR product, this fragment can be separated by a method such as agarose gel electrophoresis, which screens DNA fragments according to their molecular weights, and then isolated according to a standard method such as a method for cutting out a certain band.

Because its amino acid sequence is expected, from a predicted amino acid sequence (SEQ ID NO: 2), to have a transmembrane region at the N-terminus, the nucleic acid of the present invention that encodes a solubilized form of a polypeptide can also be obtained by preparing a region of a nucleotide sequence encoding a polypeptide without the transmembrane region. In actual experiments conducted by the present inventors, the removal of a region from the N-terminus to the 26th to 33rd amino acid of the amino acid sequence allowed the preparation of a polypeptide having an enzyme activity of interest. Thus, a nucleic acid consisting of a nucleotide sequence from nucleotide Nos. 76 to 1194 or from nucleotide Nos. 97 to 1194 in SEQ ID NO: 1 is considered to contain a region encoding an active domain region of the enzyme protein.

A homologous nucleic acid cloned using the hybridization and nucleic acid amplification reaction described above has at least 50% identity, preferably at least 60% identity, more preferably at least 70% or more identity, even more preferably at least 80% identity, still more preferably at least 90% or more identity, most preferably at least 95% identity, to the nucleotide sequence described in SEQ ID NO: 1. The nucleic acid of the present invention is a nucleic acid encoding a β1,3-N-acetylglucosaminyltransferase protein. In addition to a nucleic acid having the nucleotide sequence described in SEQ ID NO: 1, a nucleic acid encoding a protein (or a portion thereof) that is similar in activity, function, property, or the like, also comes within the scope of the present invention. The activity, property, or the like, of a protein of the present invention is described below in detail in Section (5) G9 enzyme protein of the present invention. The nucleic acid of the present invention has the closest identity to a β1,3GlcNAc transferase 2 gene that is a nucleic acid encoding a β1,3-N-acetylglucosaminyltransferase protein known in the art, and the identity of these two nucleic acids is 31% in the total length and 51% in the active domain (corresponding to SEQ ID NO: 17 of the present invention). Accordingly, a nucleic acid that has, preferably at least 55% identity to the nucleotide sequence described in SEQ ID NO: 1 and encodes a β1,3-N-acetylglucosaminyltransferase protein having a similar property comes within the scope of the present invention.

It is possible to determine the percentage of identity by visual inspection and mathematical calculation. Or otherwise, the percentage of identity of two nucleic acid sequences can be determined by using the GAP computer program, version 6.0 described in Devereux et al., Nucl. Acids Res. 12: 387, 1984 and available from the University of Wisconsin Genetics Computer Group (UWGCG) to compare sequence information. Preferred default parameters for the GAP program include: (1) a unary comparison matrix (containing a value of 1 for identity and 0 for non-identity) for nucleotide and the weighted comparison matrix of Gribskov and Burgess, Nucl. Acids Res. 14: 6745, 1986 as described in Schwartz and Dayhoff, eds., Atlas of Protein Sequence and Structure, pp. 353-358, National Biomedical Research Foundation, 1979; (2) a penalty of 3.0 for each gap and an additional penalty of 0.10 for each symbol in each gap; and (3) no penalty for end gaps. Other programs of sequence comparison used by those skilled in the art are also available.

(4) Vectors and Transformants of the Present Invention

According to the present invention, a recombinant vector containing the above-described nucleic acid that has been isolated is provided. An example of a method for incorporating a DNA fragment of the nucleic acid into a vector such as a plasmid includes a method described in Sambrook, J. et al., Molecular Cloning, A Laboratory Manual (3rd edition), Cold Spring Harbor Laboratory, 1.1 (2001). Conveniently, a commercially-available ligation kit (e.g., from TAKARA SHUZO) can also be used. The recombinant vector (e.g., the recombinant plasmid) thus obtained is introduced into a host cell (e.g., *E. coli* DH5aαTB1, LE392, or XL-LE392 or XL-1Blue).

A method for introducing a plasmid into a host cell includes a calcium chloride method or calcium chloride/rubidium chloride method, an electroporation method, an electroinjection method, a method by chemical treatment such as PEG, and a method using a gene gun or the like, described in Sambrook, J. et al., Molecular Cloning, A Laboratory Manual (3rd edition), Cold Spring Harbor Laboratory, 16.1 (2001).

The vector can be prepared simply by ligating a desired gene with a vector for recombination (e.g., plasmid DNA) available in the art according to a standard method. Concrete examples of the vector used include, but are not limited to, pDONR201, pBluescript, pUC18, pUC19, and pBR322 as a plasmid derived from *E. coli*.

Those skilled in the art can appropriately select restriction ends to be compatible with an expression vector. Those skilled in the art can appropriately select an expression vector suitable for a host cell desired to express the enzyme of the present invention. Thus, it is preferred that the expression vector according to the present invention should be constructed so that regions involved in gene expression (such as promoter, enhancer, and operator regions) are properly arranged to allow the expression of the nucleic acid in a host cell of interest and the nucleic acid is properly expressed. The construction of the expression vector can also employ a Gateway system (Invitrogen) which does not require restriction treatment and ligation procedures. The Gateway system is a system utilizing site-specific recombination, which allows the cloning of a PCR product while maintaining its orientation and also allows the subcloning of a DNA fragment into an expression vector properly modified. Specifically, an entry clone is created from a PCR product and a donor vector with a BP clonase, a site-specific recombinase, and the PCR product is then transferred to a destination vector that is capable of undergoing recombination between the destination vector and the entry clone through another recombinase LR clonase, thereby preparing an expression clone compatible with an expression system. One of the features of the Gateway system is that, once an entry clone is initially created, no laborious subcloning step having procedures with restriction enzymes and ligases is required.

The type of an expression vector is not particularly limited as long as the expression vector has the function of expressing a desired gene in a variety of prokaryotic and/or eukaryotic host cells to produce a desired protein. Examples of a preferred expression vector include: pQE-30, pQE-60, pMAL-C2, pMAL-p2, and pSE420 for *E. coli*; pYES2 (*Saccharomyces*), and pPIC3.5K, pPIC9K, and pA0815 (*Pichia*) for yeast; and pFastBac, pBacPAK8/9, pBK283, pVL1392, and pBlueBac4.5 for insects.

The incorporation of the expression vector of the present invention into a host cell can give a transformant. The host cell may be a eukaryotic cell (such as a mammalian cell, yeast, and an insect cell) or may be a prokaryotic cell (such as *E. coli* and *B. subtilis*). A host cell for obtaining the transformant of the present invention is not particularly limited and may also be a cultured cell derived from humans (e.g., HeLa, 293T, and SH-SY5Y), mice (e.g., Neuro2a, NIH3T3), and so on. Any of these are known in the art and are commercially available (e.g., from DAINIPPON PHARMACEUTICAL) or available from public research institutes (e.g., RIKEN Cell Bank). Alternatively, an embryo, an organ, a tissue, or a non-human individual may also be used.

Incidentally, the nucleic acid of the present invention is a nucleic acid found in a human genome library. Therefore, in the present invention, by using a eukaryotic cell as a host cell for the transformant of the present invention, the "nucleic acid of the present invention" having a property close to that of a natural one (e.g., morphology having the addition of an oligosaccharide) will be obtained. Thus, it is preferable to select a eukaryotic cell, especially a mammalian cell, as the "host cell". The mammalian cell is concretely exemplified by a mouse-derived cell, and an animal cell is exemplified by a mouse-derived, Xenopus laevis-derived, rat-derived, hamster-derived, monkey-derived, or human-derived cell or cultured cell lines established from those cells. *E. coli*, yeast, or an insect cell used as a host cell is concretely exemplified by DH5α, M15, JM109, and BL21 (*E. coli*); INVSc1 (*Saccharomyces*), and GS115 and KM 71 (*Pichia*) (yeast); and Sf21, BmN4, and silkworm larva (insect cell).

When a bacterium, especially *E. coli*, is used as the host cell, an expression vector is generally composed of at least a promoter/operator region, an initiation codon, a gene encoding a desired protein, a termination codon, a terminator, and a replicable unit.

When yeast, a plant cell, an animal cell, or an insect cell is used as a host cell, it is preferred that an expression vector should generally contain at least a promoter, an initiation codon, a gene encoding a desired protein, a termination codon, and a terminator. For example, DNA encoding a signal peptide, an enhancer sequence, 5'- and 3'-untranslated regions of a desired gene, a selective marker region, or a replicable unit may optionally be contained therein.

In the vector of the present invention, the preferred initiation codon is exemplified by a methionine codon (ATG). Moreover, the termination codon is exemplified by a termination codon regularly used (e.g., TAG, TGA, and TAA).

The replicable unit means DNA having the ability to replicate its total DNA sequence in a host cell and includes a natural plasmid, an artificially-modified plasmid (plasmid prepared from a natural plasmid), and a synthetic plasmid. The preferred plasmid includes: a plasmid pQE30, pET, or pCAL, or artificially-modified products thereof (DNA fragments obtained by treating pQE30, pET, or pCAL with an appropriate restriction enzyme) for *E. coli*; a plasmid pYES2 or pPIC9K for yeast; and a plasmid pBacPAK8/9 for an insect cell.

Any of those usually used by those skilled in the art such as enhancer and terminator sequences each derived from SV40 can be used as enhancer and terminator sequences.

Any of those usually used can be used as a selective marker according to a standard method. An example thereof, includes a gene resistant to an antibiotic such as tetracycline, ampicillin, or kanamycin or neomycin, hygromycin, or spectinomycin.

The expression vector can be prepared by consecutively and circularly ligating at least the above-described promoter, initiation codon, gene encoding a desired protein, termination codon, and terminator region with an appropriate replicable unit. On this occasion, an appropriate DNA fragment (e.g., a linker, other restriction sites) can be used, if desired, according to a standard method such as digestion with a restriction enzyme and ligation using a T4 DNA ligase.

The introduction [transformation (transfection)] of the expression vector of the present invention into a host cell can be carried out using a method conventionally known in the art.

The expression vector can be transformed into, for example, a bacterium (such as *E. coli* and *Bacillus subtilis*) by, for example, a method of Cohen et al. [Proc. Natl. Acad. Sci. USA, 69, 2110 (1972)], a protoplast method [Mol. Gen. Genet., 168, 111 (1979)], and a competent method [J. Mol. Biol., 56, 209 (1971)], into *Saccharomyces cerevisiae* by, for example, a method of Hinnen et al. [Proc. Natl. Acad. Sci. USA, 75, 1927 (1978)] and a lithium method [J. B. Bacteriol., 153, 163 (1983)], into a plant cell by, for example, a leaf disk method [Science, 227, 129 (1985)] and an electroporation method [Nature, 319, 791 (1986)], into an animal cell by, for example, a method of Graham [Virology, 52, 456 (1973)], and into an insect cell by, for example, a method of Summer et al. [Mol. Cell Biol., 3, 2156-2165 (1983)], respectively.

(5) Isolation and Purification of Enzyme Protein According to the Present Invention In recent years, an approach in which a transformant is cultured and grown and a substance of interest is isolated and purified from the cultured and grown products has been established as a genetic engineering approach.

The enzyme protein according to the present invention can be expressed (produced), for example, by culturing a transformant containing the expression vector prepared as described above in a nutrient medium. Preferably, the nutrient medium contains a carbon source, an inorganic nitrogen source, or an organic nitrogen source necessary for the growth of a host cell (transformant). The carbon source is exemplified by glucose, dextran, soluble starch, sucrose, and methanol. The inorganic nitrogen source or organic nitrogen source is exemplified by ammonium salts, nitrates, an amino acid, corn steep liquor, peptone, casein, a meat extract, soy bean cake, and a potato extract. The nutrient medium may also contain other nutrients (e.g., an inorganic salt (e.g., NaCl, calcium chloride, sodium dihydrogenphosphate, and magnesium chloride), vitamins, an antibiotic (e.g., tetracycline, neomycin, ampicillin, and kanamycin)), if desired. Culture is carried out by a method known in the art. Such culture conditions as temperature, pH of a medium, and culture time are appropriately selected to produce the protein according to the present invention in large amounts.

The protein according to the present invention can be acquired from a cultured product obtained by the culture described above, as follows: when the protein according to the present invention is accumulated within a host cell, the host cell is collected by a procedure such as centrifugation and filtration and then suspended in an appropriated buffer (e.g., a buffer such as Tris, phosphate, HEPES, and MES buffers having a concentration of approximately 10 to 100 mM; pH is preferably in the range of 5.0 to 9.0, which differs depending on a buffer used), followed by the disruption of the cell by a method suitable for the host cell used to obtain contents of the host cell by centrifugation; whereas, when the protein according to the present invention is secreted to the outside of a host cell, the host cell is separated from a medium by a procedure such as centrifugation and filtration to obtain a culture filtrate. A host cell disruption solution or culture filtrate can be subjected to the isolation and purification of the protein either directly or after subjecting to ammonium sulfate precipitation and dialysis. A method of isolating and purifying the protein can include the following methods: a method by affinity chromatography suitable for each tag generally used when the protein is attached to a tag such as 6× histidine, GST, or a maltose-binding protein; or alternatively a method that will be described in detail in Examples below, that is, a method by ion exchange chromatography, when the protein according to the present invention is produced without such a tag. In addition, the method can also include a method combining gel filtration, hydrophobic chromatography, isoelectric chromatography, and so on.

The enzyme protein according to the present invention is allowed to act on a glycoprotein, oligosaccharide, or polysaccharide, or the like, thereby transferring a certain sugar residue. Thus, the enzyme according to the present invention can be used in the modification of an oligosaccharide in a glycoprotein and the synthesis of saccharides. In addition, by administering this enzyme as an immunogen to an animal, an antigen against the enzyme can be created, which can in turn be used to measure the enzyme by immunoassay. Thus, the enzyme and the nucleic acid encoding the enzyme according to the present invention are useful for creating such an immunogen. Because an oligosaccharide structure synthesized by this enzyme seems to be increased in a cancer cell, an antibody against this oligosaccharide is probably available as a tumor marker. Among antibodies against an oligosaccharide, for example, CA19-9 is well known to be useful as a tumor marker. Similarly, an oligosaccharide structure capable of being a tumor antigen can be synthesized using the G9.

It is preferred that the expression vector of the present invention should be constructed so that the enzyme is easily isolated and purified as described above. When the enzyme is prepared by a genetic engineering technique using the expression vector according to the present invention that has been constructed to be expressed especially in the morphology of a fusion protein between a polypeptide having an enzyme activity and a labeling peptide, its isolation and purification would easily be performed.

An example of the identification (labeling) peptide described above is a peptide having the function of allowing the easy secretion/separation/purification or detection of the enzyme according to the present invention from a grown product of a transformant by expressing the enzyme according to the present invention as a fusion protein between the identification peptide and a polypeptide having an enzyme activity bound together in the preparation of the enzyme by genetic recombination. Examples of such an identification peptide include a peptide such as a signal peptide (peptide consisting of 15 to 30 amino acid residues, which is present in the N terminuses of many proteins and functions within a cell for sorting out a protein in intracellular transmembrane mechanisms: e.g., OmpA, OmpT, and Dsb), a protein kinase A, a protein A (protein having a molecular weight of approximately 42,000, which is a component of the cell wall of *Staphylococcus aureus*), a glutathion S-transferase, a His tag (sequence where 6 to 10 histidine residues are aligned and arranged), a myc tag (13-amino acid sequence derived from a cMyc protein), a FLAG peptide (analytical marker consisting of 8 amino acid residues), a T7 tag (which consists of the first 11 amino acid residues in a gene 10 protein), a S tag (which consists of 15 amino acid residues derived from pancreatic RNase A), a HSV tag, pelB (22-amino acid sequence in an *E. coli* outer membrane protein pelB), a HA tag (which consists of 10 amino acid residues derived from hemaglutinin), a Trx tag (thioredoxin sequence), a CBP tag (calmodulin-binding peptide), a CBD tag (cellulose-binding domain), a° CBR tag (collagen-binding domain), β-lac/blu (β lactamase), β-gal (β galactosidase), luc (luciferase), HP-Thio (His-patch thioredoxin), HSP (heat shock peptide), Lnγ (laminin γ peptide), Fn (partial peptide of fibronectin), GFP (green fluorescent peptide), YFP (yellow fluorescent peptide), CFP (cyan fluorescent peptide), BFP (blue fluorescent peptide), DsRed and DsRed2 (red fluorescent peptides), MBP (maltose-binding peptide), LacZ (lactose operator), IgG (immunoglobulin G), avidin, and a protein G, and any of these identification peptides may be used. Among them, especially the signal peptide, protein kinase A, protein A, glutathione S-transferase, His tag, myc tag, FLAG peptide, T7 tag, S tag, HSV tag, pe1B or HA tag is preferred because the enzyme according to the present invention is expressed and purified more easily according to a genetic engineering approach. It is particularly preferable to obtain the enzyme according to the present invention as a fusion protein with the FLAG peptide (Asp-Tyr-Lys-Asp-Asp-Asp-Asp-Lys) (SEQ ID NO: 6), because of considerably excellent handling ease. The FLAG peptide is highly antigenic, and it provides an epitope reversibly bound by a specific monoclonal antibody and allows the rapid assay and easy purification of a recombinant protein expressed. A murine hybridoma designated as 4E11 produces a monoclonal antibody that binds to the FLAG peptide in the presence of a certain divalent metal cation, as described in U.S. Pat. No. 5,011,912 (incorporated herein by reference). The 4E11 hybridoma cell line is deposited in American Type Culture Collection under Accession No. HB 9259. The monoclonal antibody binding to the FLAG peptide is available from Eastman Kodak Co., Scientific Imaging Systems Division, New Haven, Conn.

A basic vector capable of being expressed in a mammalian cell and yielding the enzyme according to the present invention as a fusion protein with the FLAG peptide is, for example, pFLAG-CMV-1 (manufactured by Sigma-Aldrich). Alternatively, a vector capable of being expressed in an insect cell is exemplified by pFBIF (a vector in which a region encoding the FLAG peptide is incorporated into pFastBac (Invitrogen): see Examples below). However, those skilled in the art can select a suitable basic vector, judging from a host cell, a restriction enzyme, an identification peptide, and so on, used in the expression of the enzyme.

(6) G9 Enzyme Protein of the Present Invention

As described above, a polypeptide having a certain enzyme activity can be isolated and purified using the G9 nucleic acid of SEQ ID NO: 1 of the present invention on the basis of a genetic engineering approach.

First, from the above point of view, a typical aspect of the protein of the present invention is a G9 enzyme protein having an amino acid sequence of SEQ ID NO: 2 predicted from the nucleic acid sequence of SEQ ID NO: 1. Specifically, this enzyme protein has activities described below.

Catalytic Reaction

The G9 enzyme protein can transfer N-acetyl-D-glucosamine (GlcNAc) from its donor substrate to its acceptor substrate through β1,3 glycosidic linkage and synthesize an oligosaccharide.

Donor Substrate Specificity:

Examples of the N-acetyl-D-glucosamine donor substrate include a sugar nucleotide having this sugar residue, for example, uridine diphosphate-N-acetylglucosamine (UDP-GlcNAc), adenosine diphosphate-N-glucosamine (ADP-GlcNAc), guanosine diphosphate-N-acetylglucosamine (GDP-GlcNAc), and cytidine diphosphate-N-acetylglucosamine (CDP-GlcNAc). The typical donor substrate is UDP-GlcNAc.

Acceptor Substrate Specificity (see Table 5):

The typical acceptor substrate exhibits a significant activity for Bz-β-lactoside and Galβ1-4GlcNAcα-pNp and a particularly strong activity for Galβ1-4GlcNAcα-pNp, of pNp-α-Glc, pNp-β-Glc, pNp-α-GlcNAc, pNp-β-GlcNAc, pNp-α-Gal, oNp-β-Gal, pNp-α-GalNAc, pNp-α-Xyl, oNp-β-Xyl, pNp-α-Fuc, Bz-α-Man, Bz-α-ManNAc, Bz-β-lactoside, GlcNAcβ1-4GlcNAcβ-BZ, Galβ1-4GlcNAcα-pNp.

In the present specification, "GlcNAc" represents a N-acetyl-D-glucosamine residue; "GalNAc" represents a N-acetyl-D-galactosamine residue; "ManNAc" represents a N-acetyl-D-mannosamine residue; "Glc" represents a glucose residue; "Man" represents a mannose residue; "Gal" represents a galactose residue; "Bz" represents a benzyl group; "pNp" represents a paranitrophenyl group; "oNp" represents an orthonitrophenyl group; and "-" represents glycosidic linkage. The number in the formula represents a carbon number of glycosidic linkage present in the oligosaccharide. Besides, "α" and "β" represent anomers of the glycosidic linkage at position 1 of the sugar ring, and the anomer trans to $CH_2OH$ or $CH_3$ at position 5 and the anomer cis thereto in positional relationship are expressed by "α" and "β", respectively.

Thus, the G9 enzyme protein of the present invention catalyzes reaction given by, for example, the following formula:

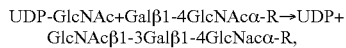
UDP-GlcNAc+Galβ1-4GlcNAcα-R→UDP+
GlcNAcβ1-3Galβ1-4GlcNacα-R, wherein R is a glycoprotein, glycolipid, oligosaccharide, or polysaccharide, or the like, having the GlcNAc residue.

Figure 4:
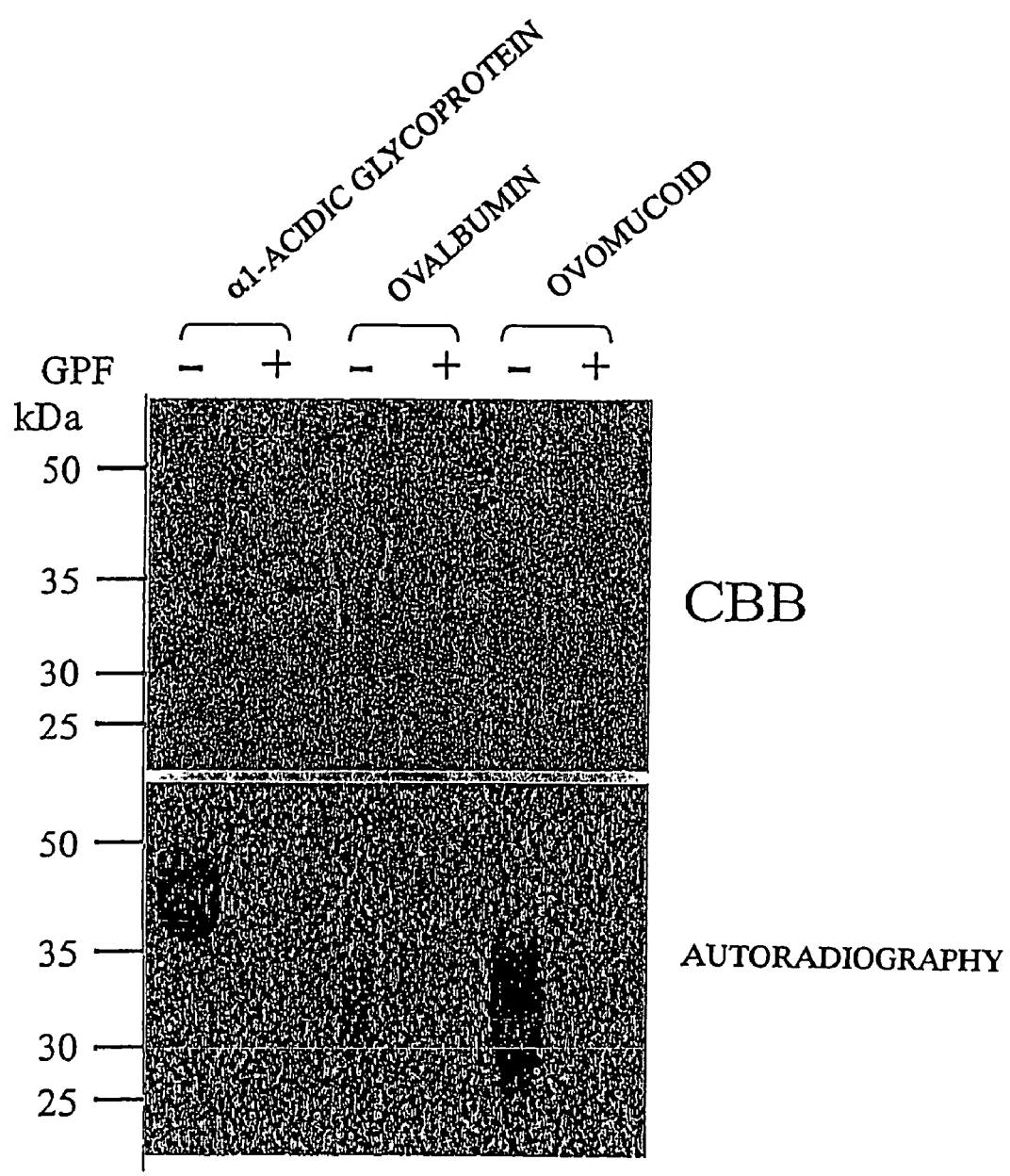
FIG. 4 is an electrophoretic picture showing activity measurement when an α1-acidic glycoprotein (orosomucoid), ovalbumin, and ovomucoid are used as acceptor substrates. The reaction mixture of an enzyme with the substrate is treated either without glycopeptidase F (−) or with glycopeptidase F (+), followed by separation by SDS-PAGE. The gel is either stained with CBB (Coomassie Brilliant Blue) (upper picture) or subjected to autoradiography (lower picture).

The G9 enzyme protein of the present invention exhibits the transferring activity for an oligosaccharide (e.g., oligosaccharide pyridylaminated with 2-aminopyridine) or a glycoprotein having an oligosaccharide residue. The G9 enzyme protein exhibits a significantly strong activity or a selectively significant activity for especially a substrate having the oligosaccharide residue in a quadruple-stranded form at the nonreducing end of an N-linked oligosaccharide (see FIGS. 3 and 4).

Optimum Buffer and Optimum pH (see FIG. 2A):

The G9 enzyme protein has the above-described catalysis in both sodium cacodylate and HEPES buffers. Generally, it has a high activity at or around neutral. Concerning the pH dependence of an activity in each of the buffers, the G9 enzyme protein has an activity that rises with an increase in pH within the neutral region from pH 6.4 to 7.2 in the sodium cacodylate buffer and shows the maximum activity around pH 7.0 in the HEPES buffer.

Divalent ion Requirement (see FIG. 2B):

The activity of the human G9 protein is significantly enhanced in the presence of at least Mn ion or Co ion among divalent metal ions and particularly remarkably enhanced in the presence of Mn ion. These enhanced activities rapidly rise in the low concentration region of the ion and subsequently gradually decrease. Although Cd and Ni ions show slight enhancing effect in the low concentration region, no enhancing effect is substantially observed in Mg and Zn ions. Usually, most of glycosyltransferases requiring a divalent ion have reaction enhanced in the presence of Mn ion.

As described above, the G9 enzyme protein of the present invention can transfer a GlcNAc residue to a certain oligosaccharide through β1,3 glycosidic linkage under the given enzyme reaction conditions described above and as such, is useful in the synthesis or modification reaction of an oligosaccharide of a glycoprotein or the like.

Second, in the present specification, the disclosure of the amino acid sequence described in SEQ ID NO: 2 that represents the primary structure of the above-described protein provides every type of protein that can be produced by a genetic engineering approach well known in the art on the basis of the amino acid sequence (hereinafter, also referred to as a "mutant protein" or "modified protein"). That is, the enzyme protein of the present invention is not limited to a protein consisting of the predicted amino acid sequence of SEQ ID NO: 2 according to common general technical knowledge in the art and as illustrated below, is intended to include a protein consisting of a polypeptide being not full-length that partially lacks, for example, the N-terminal side of the amino acid sequence, or even a protein with an amino acid sequence homologous to those amino acid sequences, which has intrinsic properties of the proteins.

Initially, the human G9 enzyme protein of the present invention can be composed of preferably an amino acid sequence described in SEQ ID NO: 16 (amino acid sequence from amino acid No. 26 to the C terminus in SEQ ID NO: 2), more preferably an amino acid sequence described in SEQ ID NO: 17 (amino acid sequence from amino acid No. 33 to the C terminus in SEQ ID NO: 2), as has been obtained in the example below.

In general, it is well known that a protein having physiological activities such as an enzyme can maintain the physiological activities even if one or several amino acid(s) is(are) substituted or deleted in any of the above-described amino acid sequences or one or several amino acid(s) is(are) inserted or added to any of the amino acid sequences. It is also known that there exist mutant proteins among native proteins, which have the mutation of one or several amino acid(s) due to the variety of living species producing them, gene mutation caused by variations in ecotype, or the presence of greatly similar isozymes, or the like. From this point of view, the protein of the present invention also includes a mutant protein that has an amino acid sequence comprising each amino acid sequence shown in SEQ ID NO: 2, 16, or 17 in which one or several amino acid(s) is(are) substituted or deleted or to which one or several amino acid(s) is(are) inserted or added, and has an activity of transferring a GlcNAc residue to a Gal residue through β1,3-glycosidic linkage under a certain enzyme reaction conditions described above. In addition, the particularly preferred modified protein includes a protein that has an amino acid sequence comprising each amino acid sequence shown in SEQ ID NO: 2 in which one or several amino acid(s) is(are) substituted or deleted or to which one or several amino acid(s) is(are) inserted or added.

In the description above, "several" refers to preferably 1 to 200, more preferably 1 to 100, even more preferably 1 to 50, most preferably 1 to 20. In general, the numbers of amino acids that can be substituted with the activity of the original protein maintained when an amino acid is substituted by site-specific mutation is preferably 1 to 10.

Moreover, the modified protein of the present invention includes a modified protein obtained by the substitution of an amino acid by another having a property similar thereto. That is, an approach for creating a recombinant protein having desired mutation by introducing the substitution of an amino acid by another having a property similar thereto (e.g., the substitution of a hydrophobic amino acid by another hydrophobic amino acid, the substitution of a hydrophilic amino acid by another hydrophilic amino acid, the substitution of an acidic amino acid by another acidic amino acid, or the substitution of a basic amino acid by another basic amino acid) is well known to those skilled in the art, and most of the modified proteins thus obtained have properties similar to those of the original proteins. From this point of view, a modified protein allowed to have such amino acid substitution is also encompassed by the present invention.

In addition, the modified protein of the present invention may be a glycoprotein in which an oligosaccharide binds to the polypeptide as long as it has the amino acid sequence as described above and has an enzyme activity intrinsic to an enzyme of interest.

When the amino acid sequence of the present invention is subjected to an identity search provided by GENETYX for identifying the range of the homologous protein of the present invention, it is understood that the amino acid sequence has the highest identity to that of a β1,3-N-acetylglucosaminyl transferase 2 protein known in the art, and that the identity of these two amino acid sequences is 37% in the total length and 39% in the active domain (which corresponds to SEQ ID NO: 17). From this point of view, an amino acid sequence preferred as the homologous protein of the present invention may generally have at least 40% identity, more preferably at least 50% identity, particularly preferably at least 60% identity to the amino acid sequence shown in SEQ ID NO: 2, 16, or 17. The β1,3-N-acetylglucosaminyltransferase protein having a property similar to those of proteins having the amino acid sequences comes within the scope of the present invention.

The GENETYX is genetic information processing software for nucleic acid analysis and protein analysis and is capable of signal peptide prediction, promoter site prediction, and secondary structure prediction in addition to usual homology analysis and multi-alignment analysis. The homology analysis program used herein adopts Lipman-Pearson method (Lipman, D. J. & Pearson, W. R., Science, 277, 1435-1441 (1985)) that is frequently used as a method with high throughput and high sensitivity.

In the present specification, percentage of identity may be determined by the comparison with sequence information using, for example, a BLAST program described by Altschul et al. (Nucl. Acids. Res., 25. 3389-3402 (1997)) or FASTA described by Pearson et al. (Proc. Natl. Acad. Sci. USA, 2444-2448 (1988)). The programs are available on the Internet from the website of National Center for Biotechnology Information (NCBI) or DNA Data Bank of Japan (DDBJ). A variety of conditions (parameters) for an identity search provided by each of the programs are described in detail in the website. Although a part of the configurations can appropriately be altered, the search is generally conducted using default values. It is noted that other sequence comparison programs used by those skilled in the art may also be employed.

Third, as described below, the isolated protein of the present invention can be administered as an immunogen to an animal to thereby produce an antibody against the protein. The enzyme can be measured and quantified by immunoassay using such an antibody. Thus, the present invention is useful for creating such an immunogen. From this point of view, the protein of the present invention includes a polypeptide fragment, a mutant, and a fusion protein from the protein, which contains an antigenic determinant or epitope for eliciting the formation of an antibody.

(7) Antibody Recognizing Protein According to the Present Invention

In the present specification, an antibody immunoreactive to a glycosyltransferase protein encoded by the nucleic acid of the present invention is provided. Such an antibody specifically binds to the glycosyltransferase protein via the antigen-binding site of the antibody (in contrast to non-specific binding). Thus, the protein of SEQ ID NO: 2, 16, or 17, or a fragment, mutant, or fusion protein thereof, or the like, as described above may be used as an "immunogen" for producing an antibody immunoreactive thereto. To be more specific, the protein, the fragment, mutant, and fusion protein thereof, and so on, contain an antigenic determinant or epitope for eliciting the formation of an antibody. The antigenic determinant or epitope may be either linear or conformational (interrupted). The antigenic determinant or epitope may be identified by any method known in the art.

Thus, one aspect of the present invention relates to an antigenic epitope of a glycosyltransferase protein encoded by the nucleic acid of the present invention. Such an epitope is useful for creating an antibody, especially a monoclonal antibody, as more fully described below. Furthermore, the epitope of the glycosyltransferase protein according to the present invention may be used in assay and as a research reagent for purifying an antibody specifically bound with the epitope from a substance such as a supernatant derived from polyclonal serum or a cultured hybridoma. Such an epitope or a mutant thereof can be produced using a technique known in the art such as solid phase synthesis and chemical or enzymatic cleavage of a protein, or using a recombinant DNA technique.

For an antibody likely to be induced by the glycosyltransferase protein, both polyclonal and monoclonal antibodies can be prepared by a routine technique even if the whole protein or a portion thereof is isolated or the epitope is isolated. See, e.g., Kennet et al., ed., Monoclonal Antibodies, Hybridomas: A New Dimension in Biological Analyses, Plenum Press, New York, 1980.

The present specification is also directed to a hybridoma cell line that produces a monoclonal antibody specific to the glycosyltransferase protein of the present invention. Such a hybridoma can be produced and identified by a routine technique. One method for producing such a hybridoma cell line comprises: immunizing an animal with the glycosyltransferase protein; collecting spleen cells from the immunized animal; fusing the spleen cells with myeloma cell lines to thereby produce hybridoma cells; and identifying a hybridoma cell line producing a monoclonal antibody that binds to the enzyme. The monoclonal antibody can be collected by a routine technique.

The monoclonal antibody according to the present invention includes a chimeric antibody, for example, a humanized murine monoclonal antibody. When such a humanized antibody is prepared by a known technique and the antibody is administered to a human, an advantage of reduced immunogenicity may be provided.

An antigen-binding fragment of an antibody, which can be produced by a routine technique, is also encompassed by the present invention. Examples of such a fragment include, but are not limited to, Fab and F(ab')$_2$. An antibody fragment and a derivative produced by a genetic engineering technique are also provided.

The antibody according to the present invention can be used in assay for detecting the presence of the glycosyltransferase protein or a fragment thereof either in vitro or in vivo. The antibody can also be employed when the polypeptide of the present invention or a fragment thereof is purified by immunoaffinity chromatography.

Furthermore, the use of a binding partner, for example, an antibody capable of blocking the binding of the glycosyltransferase protein to an acceptor substrate allows the inhibition of a biological activity generated from such binding. Such a blocking antibody may be identified using any suitable assay method such as the test of antibody for the ability to inhibit the binding of the protein to a certain cell in which an acceptor substrate is being expressed. Alternatively, the blocking antibody can be identified in assay for the ability to inhibit biological influence arising from the enzyme according to the present invention bound with a binding partner for a target cell.

By using such an antibody an in vitro method or administering the antibody in vivo, a biological activity mediated by an entity producing the antibody can be inhibited. Thus, it is possible to treat disorders caused or deteriorated (directly or indirectly) by the interaction between the glycosyltransferase protein of the present invention and a binding partner. The therapy involves administrating, to a mammal in vivo, the blocking antibody in an effective amount for inhibiting a binding partner-mediated biological activity. In general, a monoclonal antibody is preferred for use in such therapy. In one aspect, an antigen-binding antibody fragment is used.

(8) Finding of Murine G9 and Construction of Genetically-Engineered Animal

As the above-described human G9 has been found, the present inventors have conducted a search from a gene database using a BLAST search and so on and consequently detected the presence of murine orthologs of the human G9 (SEQ ID NOs: 18 to 20).

A murine G9 nucleic acid has been found as a nucleic acid having ORF with 1170 bases in length (SEQ ID NO: 19) in a sequence with a total of 1845 bases in length (SEQ ID NO: 18). This ORF is estimated to encode an amino acid sequence (SEQ ID NO: 20) of a murine β1,3-N-acetyl-D-glucosaminyltransferase protein consisting of 389 amino acid residues. In the present specification, every investigation and deliberation conducted on the human G9 can similarly be applied to the murine G9.

Based on the finding of the murine G9, the present invention also provides means for the expression and function analysis of the G9 at the animal individual level which is based on a variety of gene conversion techniques using fertilized eggs and ES cells and typically provides even a transgenic animal into which the G9 gene is introduced and a knockout mouse that is deficient in the murine G9.

For example, the knockout mouse can be constructed according to a standard method in the art (see e.g., The Latest Techniques for Gene Targeting, K. Yagi, ed., YODOSHA; Gene Targeting, supervisory for translation by T. Noda, MEDICAL SCIENCES INTERNATIONAL). That is, those skilled in the art can acquire a homologously recombinant ES cell of the murine G9 (mG9) according to a gene targeting method known in the art using the sequence information of murine G9 nucleic acid disclosed in the present application and can construct a G9 knockout mouse using the ES cell (see Example 6).

Alternatively, a method for suppressing gene expression by a small interfering RNA method has recently been developed (T. R. Brummelkamp et al., Science, 296, 550-553 (2002)), and the G9 knockout mouse can be constructed according to such a method known in the art.

Providing the G9 knockout mouse would be helpful in elucidating the involvement of the G9 gene in a certain life phenomenon, that is, information on the redundancy of the gene as well as the relationship between the deficiency of the gene and a phenotype (including every type of abnormality for motion, intelligence, and sensory function) at an individual level and even the function of the gene in individual lifecycle such as development, growth, and aging. To be more specific, the knockout mouse obtained by the above-described method can be used to investigate the detection of the carriers of oligosaccharides synthesized by the G9 and mG9 and the relationship with physiological function and disease, and so on. For example, a glycoprotein and a glycolipid are extracted from each tissue excised from the knockout mouse and compared with those from a wild-type mouse by a technique such as proteomics (e.g., two-dimensional electrophoresis, two-dimensional thin-layer chromatography, and mass spectrometry) to thereby allow the identification of the carriers of the synthesized oligosaccharides. Moreover, the comparison of phenotypes (e.g., fetation, growth process, and spontaneous behavior) between the knockout mouse and a wild-type mouse allows the estimation of the relationship with physiological function and disease.

Hereinafter, the present invention will be described more fully with reference to examples. However, the present invention is not intended to be limited to examples described below.

EXAMPLES

Example 1

Cloning of DNA of the Present Invention

As a result of searching a gene having homology to a β1,3-N-acetylglucosaminyltransferase gene or a gene likely to encode a protein having homology to the enzyme at an amino acid level from a gene database using programs such as Blast [Altschul et al., J. Mol. Biol. 215, 403-410 (1990)], the FASTA method, the PSI-BLAST method, and the FrameSearch method [manufactured by Compugen], a human genome DNA sequence (AC011462: Homo sapiens chromosome 19 clone CTC-435M10) and a EST (AW444713) sequence, and the like were found. A polypeptide encoded by each of these sequences is considered to be a homolog protein of the β1,3-N-acetylglucosaminyltransferase and was designated as G9.

Unless otherwise specified in the description below, a method known in the art which is described in Molecular Cloning 2nd Ed. was used as a genetic engineering approach.

RNA was extracted from a colorectal cancer cell line colo 205 with RNeasy Mini Kit (manufactured by Qiagen) to synthesize single strand DNA by an oligo(dT) method using Super-Script First-Strand Synthesis System (manufactured by Invitrogen). This DNA was used as a template to carry out PCR with a 5' primer (SEQ ID NO: 3) and a 3' primer (SEQ ID NO: 4). PCR conditions comprised 25 cycles, each cycle having 94° C. for 30 seconds, 65° C. for 1 minute, and 72° C. for 1 minute. A DNA fragment obtained by PCR has, as restriction sites, HindIII on the 5' side of the initiation codon of ORF and EcoRI on the 3' side of the stop codon thereof.

This DNA fragment and pBluescript(R) II SK(−) (manufactured by TOYOBO) were individually treated with restriction enzymes HindIII and EcoRI, with which a reaction solution was then mixed, followed by ligation reaction to thereby introduce the ORF of the G9 into the pBluescript(R) II SK(−). The reaction solution was purified by an ethanol precipitation method and then mixed with a competent cell (E. coli DH5α). The mixture was subjected to a heat shock method (42° C., 30 sec.) and seeded to a LB agar medium containing IPTG and X-gal. The next day, a single white colony was further cultured to collect plasmid DNA.

The collected plasmid DNA was confirmed to contain the nucleic acid sequence of interest and the nucleotide sequence was determined (SEQ ID NO: 1). A predicted open reading frame (ORF) in that nucleotide sequence is 1194 bp, and its predicted amino acid sequence consists of 397 amino acids (SEQ ID NO: 2). The predicted amino acid sequence has a hydrophobic amino acid region characteristic of a glycosyltransferase at its N terminus. Those consisting of the nucleic acid sequence and the amino acid sequence were designated as G9.

The pBluescript(R) II SK (−) into which the G9 is incorporated is a multifunctional vector developed for carrying out cloning procedures and sequencing procedures more conveniently and has various improvements in addition to the function of conventional pUC and M13 vectors. Because a multicloning site is contained in a LacZ gene as with the pUC vector, the plasmid incorporating an insert therein is transformed into E. coli having the genotype of lacZΔM15 such as XL1-Blue MRF' and JM109, which in turn forms a white colony in a plate supplemented with IPTG/X-gal. Thus, the presence or absence of the insert can be easily assessed. Moreover, because the multi-cloning site has a polylinker consisting of 21 restriction sites, the range of choices for restriction enzymes used are extended when a deletion mutant is created by Exo/Mung System. The incorporated G9 gene can be adjusted in its expression within E. coli having lacIq mutation through LacZ operator/promoter, and the E. coli is allowed to produce a protein of interest by the addition of IPTG to a medium. Furthermore, because T3 and T7 promoters are present on both sides of that multi-cloning site, it is possible to create RNA probes with these promoters. BssHII sites are present on both sides of each of those promoters and can be utilized to cut out inserted DNA together with the promoter sequences. Using the probes from both of the promoters, gene mapping can be carried out. Because such a vector contains the replication origin of an f1 phage, single-stranded DNA is produced by the infection of a VCSM13 or R408 helper phage and can be used in sequencing and Site Specific Mutagenesis. An antisense strand is rescued by the infection of the helper phage.

Example 2

Expression Level of DNA of the Present Invention in Human Colorectal Cancer Tissue The expression level of the G9 gene in normal and colorectal cancer tissues from identical patients were compared using a quantitative real-time PCR method.

The quantitative real-time PCR method is a method that combines sense and antisense primers with a fluorescently-labeled probe in PCR. In amplification by PCR, the fluorescent label of the probe comes off and shows fluorescence. Fluorescent intensity is amplified in correlation with the amplification of a gene and as such, used as an indicator to conduct quantification.

RNA was extracted from human colorectal cancer tissues and normal and colorectal cancer tissues from identical patients with RNeasy Mini Kit (manufactured by Qiagen) to synthesize single strand DNA by an oligo(dT) method using Super-Script First-Strand Synthesis System (manufactured by Invitrogen). This DNA was used as a template to carry out quantitative real-time PCR with ABI PRISM 7700 (manufactured by Applied Biosystems Japan) using a 5' primer (SEQ ID NO: 5), a 3' primer (SEQ ID NO: 6), and a TaqMan probe (SEQ ID NO: 7). PCR conditions comprised reaction at 50° C. for 2 minutes and 95° C. for 10 minutes, followed by cycles repeated 50 times, each cycle having 95° C. for 15 seconds and 60° C. for 1 minute. The obtained measurement values were divided by a value from β-actin as an internal standard gene quantified using a kit manufactured by Applied Biosystems Japan Ltd., in order to correct variations among individuals. Comparison was made between the measurement values of the human colorectal cancer tissues and those of the normal and colorectal cancer tissues from identical patients.

The result has demonstrated that the transcript from the DNA of the present invention is not present or is too negligible to measure in the non-cancerous tissues and that the transcript from the DNA of the present invention is significantly present in the cancerous tissues (see Table 3).

TABLE 3

| Patient No. | Normal tissue | Cancer tissue |
| --- | --- | --- |
| Patient 1 | 0 | 0.0052 |
| Patient 2 | 0 | 0.0004 |
| Patient 3 | 0 | 0.0023 |
| Patient 4 | 0 | 0.0012 |
| Patient 5 | 0 | 0.0018 |
| Patient 6 | 0 | 0.0028 |
| Patient 7 | 0 | 0.0007 |
| Patient 8 | 0 | 0.0057 |
| Average | 0.0000000 | 0.0025125 |

Expression Level of DNA of the Present Invention in Human Peripheral Blood

The expression level of the G9 gene in peripheral blood of normal individuals and patients with colorectal cancer was compared using a quantitative real-time PCR method.

Blood was collected into a PAXgene blood RNA tube (manufactured by PreAnalytix) from healthy volunteers and patients with colorectal cancer. After the blood was mixed by inversion with reagents in the tube and reacted at room temperature for 24 hours, RNA was extracted with a PAXgene blood RNA kit (manufactured by PreAnalytix). Using Super-Script First-Strand Synthesis System (manufactured by Invitrogen), cDNA was synthesized with accompanying random primers. This DNA was used as templates to carry out quantitative real-time PCR with ABI PRISM 7700 (manufactured by Applied Biosystems Japan) using a 5' primer (SEQ ID NO: 4), a 3' primer (SEQ ID NO: 5), and a TaqMan probe (SEQ ID NO: 6). PCR conditions comprised reaction at 50° C. for 2 minutes and 95° C. for 10 minutes, followed by cycles repeated 50 times, each cycle having 95° C. for 15 seconds and 60° C. for 1 minute. The obtained measurement values were divided by a value from β-actin as an internal standard gene quantified using a kit manufactured by Applied Biosystems Japan Ltd., in order to correct variations among individuals. Comparison was made between the normal individuals and the patients with colorectal cancer.

The result has demonstrated that the transcription level of the DNA of the present invention in the peripheral blood from the patients with colorectal cancer is significantly greater than that in the peripheral blood from the normal individuals. When patients with colorectal cancer having the measurement value that exceeds the average measurement value of normal individuals+ (standard deviation ×2) were assessed to be positive, the positive rate of the patients with colorectal cancer was 67% (see Table 4).

TABLE 4

| No. | Normal individual | Patient with colorectal cancer | Assessment |
| --- | --- | --- | --- |
| 1 | 90 | 121 | Positive |
| 2 | 107 | 68 | Negative |
| 3 | 82 | 199 | Positive |
| 4 | 81 | 418 | Positive |
| 5 | 87 | 123 | Positive |
| 6 | | 92 | Negative |
| 7 | | 196 | Positive |
| 8 | | 86 | Negative |
| 9 | | 473 | Positive |
| 10 | | 267 | Positive |
| 11 | | 110 | Positive |
| 12 | | 46 | Negative |
| Average | 89.4 | 183.3 | |
| Standard deviation | 9.4 | 132.1 | |

Expression Level of DNA of the Present Invention in a Variety of Human Normal Tissues The expression level (at cDNA) of the DNA of the present invention derived from human normal tissues was compared using a quantitative real-time PCR method in the same way as above. RNA from these tissues is commercially available from Clontech Inc., and so on. The synthesis of cDNA employed Super-Script First-Strand Synthesis System (manufactured by Invitrogen). However, pCR2.1 (Invitrogen) DNA containing a GAPDH (glyceraldehyde-3-phosphate dehydrogenase) gene was used for creating the calibration curve of an internal standard. The pBluescript(R) II SK(−) vector DNA containing the ORF of the cloned G9 nucleic acid was used for creating the calibration curve of the G9.

As a result, the expression of the DNA of the present invention is observed in most of the human normal tissues. It has revealed that the expression is relatively high in especially the bone marrow, the spleen, and the small intestine and however, the large intestine and the prostate have a considerably weak expression or substantially no expression (see FIG. 1).

Example 3

Expression of Isolated Full-Length G9

The plasmid DNA where the G9 was incorporated into the pBluescript(R) II SK(−) and pcDNA3.1 (manufactured by Invitrogen) were individually treated with restriction enzymes HindIII and EcoRI, with which a reaction solution was then mixed, followed by ligation reaction to thereby introduce the ORF of the G9 into the pcDNA3.1(+). The reaction solution was purified by an ethanol precipitation method. Then, by investigating the sequence, the G9 was confirmed to be introduced into the pcDNA3.1(+) and this was designated as pcDNA3.1(+)-G9. The pcDNA3.1(+)-G9 was mixed with a competent cell (*E. coli* DH5α). The mixture was subjected to a heat shock method (42° C., 45 sec.) and seeded to a LB agar medium containing ampicillin. The next day, a single colony was further cultured to collect plasmid DNA. The collected plasmid DNA was confirmed to contain the nucleic acid sequence of interest and the nucleotide sequence was determined.

The pcDNA3.1(±) is an expression vector for a broad variety of mammalian cells. It is a vector for forward transcription, in which a sequence likely to form the secondary structure of RNA is removed from a multi-cloning site (MCS) sequence by improving conventional pcDNA3.1 for enhancing expression level. The pcDNA3.1(±) has the enhancer/promoter of CMV and allows a high level of expression. RNA is stabilized by a polyadenylated signal and a transcription termination sequence. Because there exists a SV40 origin, the pcDNA3.1(±) can be replicated in a cell in which a SV40 Large T antigen is being expressed. An ampicillin-resistant gene is introduced therein for selection in *E. coli*. A neomycin-resistant gene is also introduced therein for selection for producing a stable strain in a mammalian cell.

HCT15 cells, human colorectal cancer-derived cell lines, were used to conduct procedures below for creating G9-expressing stable strains. The HCT15 cells were suspended at $2 \times 10^6$ cells in 10 ml of a RPMI-1640 medium containing 10% fetal bovine serum but no antibiotic, then seeded to a 10-cm dish, and cultured in a $CO_2$ incubator at 37° C. for 16 hours. The plasmid DNA (20 ng) of the pcDNA3.1(+)-G9 and 30 μl of Lipofectamine 2000 (manufactured by Invitrogen) were mixed with 1.5 ml of OPTI-MEM (manufactured by Invitrogen), respectively, and incubated at room temperature for 5 minutes. Further, these two solutions were gradually mixed and incubated at room temperature for 20 minutes. This mixture solution was added dropwise to the dish and cultured in a $CO_2$ incubator at 37° C. for 48 hours. The cells were subcultured by a standard method. On this occasion, RPMI-1640 (manufactured by Invitrogen) was used as a medium, to which fetal bovine serum, and penicillin (manufactured by Invitrogen), streptomycin (manufactured by Invitrogen), and Geneticin (neomycin; manufactured by Invitrogen) as antibiotics were added. Because cells in which the pcDNA3.1(+)-G9 has not been introduced are allowed to die out by the addition of Geneticin, continued culture results in the survival of only cells in which the pcDNA3.1(+)-G9 has been introduced. These cells were used as G9-expressing stable strains.

Expression of G9 Recombinant Protein in Mammalian Cell Line

For obtaining a G9 recombinant protein, the G9 was expressed in a human kidney-derived cell line 293T. Only the expression of an active region from the 105th amino acid to the C terminus in SEQ ID NO: 2 which relatively retains homology to at least β1,3GlcNAc transferase and β1,3Gal transferase may be adequate for investigating a function. However, here, it has been decided to express two predicted active regions from the 24th amino acid and the 33rd amino acid to the C terminus in the G9.

Using, as a template, the plasmid DNA where the G9 was incorporated into the pBluescript(R) II SK(−), PCR reaction was carried out with each of 5' primers (SEQ ID NOs: 8 and 9) and a 3' primer (SEQ ID NO: 10) to obtain a DNA fragment of interest. The PCR method comprised 25 cycles, each cycle having 94° C. for 30 seconds, 65° C. for 1 minute, and 72° C. for 1 minute. Then, a PCR product was subjected to agarose gel electrophoresis. The gel was cut out by a gel excision method to isolate the PCR product by a standard method. This PCR product had HindIII on the 5' side and EcoRI on the 3' side as restriction sites. This DNA fragment and pFLAG-CMV3 were individually treated with restriction enzymes HindIII and EcoRI, with which a reaction solution was then mixed, followed by ligation reaction to thereby introduce the DNA fragment into the pFLAG-CMV3. The reaction solution was purified by an ethanol precipitation method and then mixed with a competent cell (*E. coli* DH5α). The mixture was subjected to a heat shock method (42° C., 45 sec.) and seeded to a LB agar medium containing ampicillin.

The next day, the DNA of interest in the resulting colony was directly confirmed by PCR. After the DNA sequence was confirmed by sequencing for additional confirmation, the vector (pFLAG-CMV3) was extracted and purified.

Human kidney cell-derived cell line 293T cells were suspended at $2 \times 10^6$ cells in 10 ml of a DMEM medium containing 10% fetal bovine serum but no antibiotic, then seeded to a 10-cm dish, and cultured in a $CO_2$ incubator at 37° C. for 16 hours. The pFLAG-CMV3-G9 (20 ng) and 30 μl of Lipofectamine 2000 (manufactured by Invitrogen) were mixed with 1.5 ml of OPTI-MEM (manufactured by Invitrogen), respectively, and incubated at room temperature for 5 minutes. Further, these two solutions were gradually mixed and incubated at room temperature for 20 minutes. This mixture solution was added dropwise to the dish and cultured in a $CO_2$ incubator at 37° C. for 48 hours.

With 10 ml of the resulting culture supernatant, $NaN_3$ (0.05%), NaCl (150 ml), $CaCl_2$ (2 ml), anti-FLAG M1 affinity gel (manufactured by Sigma) (100 μl) were mixed and stirred overnight at 4° C. The next day, the mixture was centrifuged (3000 rpm, 5 min, 4° C.) to collect a pellet to which 900 μl of 2 ml $CaCl_2$/TBS was in turn added. The mixture was centrifuged again (2000 rpm, 5 min, 4° C.), and the resulting pellet was floated in 200 μl of 1 ml $CaCl_2$/TBS and used as a sample (G9 enzyme solution) for activity measurement. A portion of this was subjected to electrophoresis by SDS-PAGE and subsequently to western blotting with anti FLAG-M2 peroxidase (manufactured by Sigma), to confirm the expression of the G9 protein of interest. As a result, a band was detected at the position of approximately 45 kDa, and the expression was therefore confirmed.

Expression of G9 Recombinant Protein in an Insect Cell Line

For obtaining a G9 recombinant protein, the G9 was expressed in an insect cell. Only the expression of an active region from the 105th amino acid to the C terminus in SEQ ID NO: 2 which relatively retains homology to at least β1,3GlcNAc transferase and β1,3Gal transferase may be adequate for investigating a function. However, here, it has been decided to express a predicted active region from the 36th amino acid to the C terminus in the G9.

Using, as a template, the plasmid DNA where the G9 was incorporated into the pBluescript(R) II SK(-), PCR reaction was carried out with a 5' primer (SEQ ID NO: 11) and a 3' primer (SEQ ID NO: 12) to obtain a DNA fragment of interest. The PCR method comprised 25 cycles, each cycle having 94° C. for 30 seconds, 65° C. for 1 minute, and 72° C. for 1 minute. Then, a PCR product was subjected to agarose gel electrophoresis. The gel was cut out by a gel excision method to isolate the PCR product by a standard method. The PCR product thus isolated was incorporated into pDONR™ 201 (manufactured by Invitrogen) by BP clonase reaction to create an "entry clone".

Reaction was carried out by incubating 2 µl of the PCR product, 1 µl (150 ng) of the pDONR 201, 2 µl of a BP reaction buffer, 3 µl of a Tris-EDTA buffer (pH 8.0; hereinafter, also abbreviated to "TE"), and 2 µl of BP clonase mix at 25° C. for 1 hour. The mixture was then supplemented with 1 µl of a proteinase K (manufactured by Kaken Pharmaceutical) and incubated at 37° C. for 10 minutes to terminate the reaction. The reaction mixture solution (11 µl) was mixed with 100 µl of a competent cell (*E. coli* DH5α), then transformed by a heat shock method, and seeded to a LB plate containing kanamycin. The next day, a colony was collected to confirm the introduction of the DNA of interest and its nucleotide sequence by PCR. The vector in which the DNA was inserted (pDONR-G9) was extracted and purified according to a standard method. The nucleotide sequence of the DNA inserted in this vector was confirmed to contain the nucleotide sequence described in SEQ ID NO: 1.

Preparation of Expression Clone

The above-described entry clone has attL sites at both ends of the inserted site that are recombination sites when a λ phage is excised from *E. coli*. By mixing the entry clone with a LR clonase (mixture of λ phage recombinases Int, IHF, and Xis) and a destination vector (which has attR), the inserted site was transferred to the destination vector to generate an expression clone.

With 1 µl of the entry clone (pDONR-G9), 0.5 µl (75 ng) of the destination vector (pFBIF), 2 µl of a LR reaction buffer, 4.5 µl of TE, and 2 µl of LR clonase mix (mixture solution of λ phage recombinases Int, IHF, and Xis) were incubated at 25° C. for 1 hour. The mixture was then supplemented with 1 µl of a proteinase K (manufactured by Kaken Pharmaceutical) and incubated at 37° C. for 10 minutes to terminate the reaction (this recombination reaction yields pFBIF-G9). The pFBIF was obtained by inserting an Igκ signal sequence and a FLAG peptide for purification into pFastBac1 (manufactured by Invitrogen) according to a standard method. For further inserting the Gateway sequence (attR) into the pFBIF, Gateway Vector Conversion System (manufactured by Invitrogen) was used to insert a conversion cassette. This conversion cassette is a cassette for altering an expression vector to a destination vector and has an attR recombination site, a chloramphenicol-resistant gene, and a ccdB gene encoding a protein that inhibits an *E. coli* DNA gyrase. The Igκ signal sequence was inserted for rendering an expressed protein secretory, while the FLAG tag was inserted for facilitating purification.

The reaction mixture solution (11 µl) containing the pFBIF-G9 and 100 µl of a competent cell *E. coli* DH5α were mixed and transformed by a heat shock method, and the resulting recombinant DH5α was seeded to a LB medium containing ampicillin and then cultured. After 24-hour culture, a colony was collected, and the plasmid (pFBIF-G9) was extracted and purified by QIAprep Spin Miniprep Kit (manufactured by Qiagen). A PCR method was used to confirm the insertion of the DNA of interest.

Preparation of Bacmid by Bac-to-Bac System (Manufactured by Invitrogen)

Subsequently, using a Bac-to-Bac system (manufactured by Invitrogen), recombination was conducted between the pFBIF-G9 and a bacmid to insert the G9 sequence into the bacmid capable of proliferation in an insect cell. This system is a system that utilizes the recombination site of Tn7 and allows the incorporation of the gene of interest (G9) into the bacmid through a recombination protein produced by a helper plasmid only by introducing, into bacmid-containing *E. coli* (*E. coli* DH10Bac™), pFastBac in which the gene of interest is inserted (i.e., pFBIF-G9). Moreover, the bacmid contains a LacZ gene and is selectable by classical colony colors (blue (without insertion) to white (with insertion)).

That is, 50 µl of the above-described purified vector (pFBIF-G9) and 50 µl of a competent cell (*E. coli* DH10Bac) were mixed, then transformed by a heat shock method, and seeded to a LB medium containing kanamycin, gentamicin, tetracycline, 5-bromoindolyl-β-D-galactopyranoside (Bluogal), and isopropyl-β-D-thiogalactopyranoside (IPTG). After 24 hours, an independent white colony where the DNA of interest is inserted into the bacmid was collected and further cultured to collect the bacmid according to a standard method.

Introduction of Bacmid into Insect Cell

The insertion of the DNA of interest into the collected bacmid was confirmed according to a standard method, and the bacmid was transfected into an insect cell (Sf21; manufactured by Invitrogen). That is, a Sf900 SFM medium (manufactured by Invitrogen) containing an antibiotic was added to the Sf21 cells at $9 \times 10^5$ cells/2 ml which was then allowed to adhere to a 35-mm Petri dish at 27° C. for 1 hour. After the cells were confirmed to adhere to the Petri dish, the culture solution was aspirated. The cells were supplemented and incubated at 270 for 5 hours with a culture solution where 800 µl of Sf900II (manufactured by Invitrogen) was added to a solution of lipid-DNA complexes (solution obtained by gently mixing and incubating, at room temperature for 30 minutes, A Solution (mixture of 5 µl of the above-described bacmid added to 100 µl of Sf-900 SFM) and B Solution (mixture of 6 µl of Cellfectin Reagent (manufactured by Invitrogen) added to 100 µl of Sf-900 SFM)). Then, the medium was removed, and the cells were supplemented with 2 ml of a SF900 SFM medium containing an antibiotic and incubated 27° C. for 72 hours. After culture, the cells were liberated by pipetting. The cells and the culture solution were collected and centrifuged at 1000×g for 10 minutes to collect a supernatant (this supernatant was used as a "primary virus solution").

Further, $1 \times 10^7$ Sf21 cells/20 ml of Sf-900 SFM (containing an antibiotic) were added to a T75 culture flask and incubated at 27° C. for 1 hour. After the adhesion of the cells to the flask, 800 µl of the primary virus solution was added and cultured at 27° C. for 48 hours. After culture, the cells were liberated by pipetting. The cells and the culture solution were collected and centrifuged at 1000×g for 10 minutes to collect a supernatant (this supernatant was used as a "secondary virus solution").

Further, $1 \times 10^7$ Sf21 cells/20 ml of Sf-900 SFM (containing an antibiotic) were added to a T75 culture flask and incubated at 27° C. for 1 hour. After the adhesion of the cells to the flask, 1000 µl of the secondary virus solution was added and cultured at 27° C. for 84 hours. After culture, the cells were liberated by pipetting. The cells and the culture solution were collected and centrifuged at 1000×g for 10 minutes to collect a supernatant (this supernatant was used as a "tertiary virus solution").

In addition, 100 μl of Sf-900 SFM (containing an antibiotic) containing Sf21 cells at a concentration of 6×10$^5$ cells/ml and subsequently 1 ml of the tertiary virus solution were added to a 100-ml spinner flask and cultured at 27° C. for 96 hours. After culture, the cells and the culture solution were collected and centrifuged at 1000×g for 10 minutes to collect a supernatant (this supernatant was used as a "quaternary virus solution").

NaN$_3$, NaCl, and CaCl$_2$ were added to 10 ml of the quaternary virus solution. The final concentration is set to 0.05% for NaN$_3$, to 150 mM for NaCl, and to 2 mM for CaCl$_2$. To the mixture solution, 50 μl of anti-FLAG M1 antibody affinity gel (manufactured by Sigma) was added and gently mixed by inversion at 40C for 16 hours. Following centrifugation (1000×g, 3 min. 4° C.) to remove the resulting supernatant, the affinity gel was washed twice with TBS (Tris-buffered saline, pH 7.4) containing 1 mM CaCl$_2$. After washing, the affinity gel was suspended in 200 μl of TBS (pH 7.4) containing 1 mM CaCl$_2$, and this suspension was used as a G9 enzyme solution for activity measurement.

Example 4

Construction of G9 Enzyme Protein with Mammal Cell Expression System (1) Construction of Secretory G9 Polypeptide Recombinant As shown in the examples above, the G9 polypeptide constructed by deleting a region on the N-terminal side of the polypeptide was confirmed to be capable of being expressed as a protein in an insect cell and so on. A protein constructed as a FLAG peptide-fused G9 polypeptide by deleting a region on the N-terminal side in a similar way can also be isolated and purified as an enzyme protein having an activity by a mammalian cell expression system.

The part likely to be the catalytic region of an enzyme protein in the ORF of the G9 nucleic acid could be obtained by using, as a template, the plasmid DNA where the G9 is incorporated into the pBluescript(R) II SK(–) to carry out PCR reaction with a 5' primer having a nucleic acid sequence of either SEQ ID NO: 13 or 14 and a 3' primer having a nucleic acid sequence of SEQ ID NO: 15. The PCR method employed a Pfx Taq DNA polymerase (manufactured by Invitrogen) and comprised 25 cycles, each cycle having 94° C. for 15 seconds, 60° C. for 30 seconds, and 68° C. for 1 minute in the presence of 5 ng of the template in a total of 50 μl of a reaction solution. Then, a PCR product was subjected to agarose gel electrophoresis. The gel was cut out by a gel excision method to isolate the PCR product by a standard method.

A recombinant DNA fragment having a nucleic acid sequence from nucleotide Nos. 76 to 1194 in SEQ ID NO: 1 was obtained by PCR reaction using the 5' primer of SEQ ID NO: 13 and the 3' primer of SEQ ID NO: 15. This fragment corresponds to that encoding an amino acid sequence from amino acid Nos. 26 to 397 in SEQ ID NO: 2, that is, an amino acid sequence of SEQ ID NO: 16.

Alternatively, a recombinant DNA fragment having a sequence shorter than that of the above-described DNA fragment was obtained by PCR reaction using the 5' primer of SEQ ID NO: 14 and the 3' primer of SEQ ID NO: 15. This fragment is composed of a nucleotide sequence from nucleotide Nos. 97 to 1194 in SEQ ID NO: 1 and corresponds to that encoding an amino acid sequence from amino acid No. 33 to 397 in SEQ ID NO: 2, that is, an amino acid sequence of SEQ ID NO: 17. Although all of the polypeptides expressed from these recombinant DNA fragments were confirmed to have an enzyme activity, the longer DNA fragment obtained by the combination of the primers of SEQ ID NO: 13 and SEQ ID NO: 15 was used in the experiments below.

By adding the signal sequence of preprotrypsin and a FLAG peptide (Asp-Tyr-Lys-Asp-Asp-Asp-Asp-Lys) to the region of the G9 polypeptide as described above in which initiation methionine has been removed, the secretion and expression of a FLAG peptide-fused G9 polypeptide can be undertaken. That is, after the DNA fragment amplified with the primers was treated with restriction enzymes HindIII and EcoRI, the DNA was purified and inserted between HindIII and EcoRI in the cloning site of a pFLAG-CMV3 (manufactured by Invitrogen, Carlsbad, Calif.) vector, followed by ligation reaction to thereby create pFLAG-CMV3-G9. The reaction solution was purified by an ethanol precipitation method and then mixed with a competent cell (*E. coli* DH5α). The mixture was subjected to a heat shock method (42° C., 45 sec.) and seeded to a LB agar medium containing ampicillin. The next day, the insertion of the DNA of interest in the resulting colony was directly confirmed by PCR. After the plasmid DNA sequence was confirmed by sequencing for additional confirmation, the vector (pFLAG-CMV3-G9) was extracted and purified. As described below, the obtained recombinant DNA can be expressed as an enzyme protein and purified, and its activity can be confirmed. Here, computer prediction and preliminary experiments, and so on indicated that catalytic regions in both transmembrane and secretory forms probably had the same exon (sequence). In addition, the N-terminal side is composed of a region not required for the temporary confirmation of an activity such as a transmembrane region, so that the sequence portion as described above was used.

The pFLAG-CMV3-G9 plasmid created as above was transfected into a HEK293T cell, and the FLAG peptide-fused G9 polypeptide was expressed and secreted into a culture supernatant. The transfection method was carried out using Lipofectamine 2000 (manufactured by Invitrogen) according to the attached instruction. Specifically, human kidney cell-derived cell line 293T cells were suspended at 2×10$^6$ cells in 10 ml of a DMEM medium containing 10% fetal bovine serum but no antibiotic, then seeded to a 10-cm dish, and cultured in a CO$_2$ incubator at 37° C. for 16 hours. The pFLAG-CMV3-G9 (20 ng) and 30l of Lipofectamine 2000 (manufactured by Invitrogen) were mixed with 1.5 ml of OPTI-MEM (manufactured by Invitrogen), respectively, and incubated at room temperature for 5 minutes. Further, these two solutions were gradually mixed and incubated at room temperature for 20 minutes. This mixture solution was added dropwise to the dish and cultured in a CO$_2$ incubator at 37° C. for 48 hours.

It is noted that the portion of 372 amino acid residues described in SEQ ID NO: 16 is the portion free from the FLAG and so on in the amino acid sequence of the G9 polypeptide portion obtained as described above. On the other hand, a polypeptide portion of SEQ ID NO: 17 is obtained in a similar way, but having a slightly shorter length is contained in the sequence of SEQ ID NO: 16 and is a region consisting of 282 amino acid residues containing a region that is considered as an active domain from the viewpoint of homology, to a β1,3-N-acetyl-D-glucosaminyltransferase protein known in the art. Those containing at least this region probably show the enzyme activity of interest.

(2) Purification of G9 Polypeptide Secreted into Culture Solution

The G9 polypeptide recombinant described above is secreted and expressed as a fusion protein with the FLAG peptide and as such, can easily be purified using anti-FLAG M1 antibody affinity gel (manufactured by Sigma). The purified enzyme protein may be liberated from the anti-FLAG M1 affinity gel or otherwise may be used by being adsorbed in the gel. In the present example, the enzyme was used by being absorbed in the gel, to carry out experiments.

$NaN_3$, NaCl, and $CaCl_2$ were added to 15 ml of the culture supernatant acquired as above to be brought to 0.1%, 150 mmol/l, and 2 mmol/l, respectively, at the final concentration. The mixture was then supplemented with 100 µl of Anti-FLAG M1 Affinity Gel (manufactured by COSMO Bio) and gradually stirred overnight at 4° C.

The next day, the mixture was centrifuged (3000 rpm, 5 min, 4° C.) to collect a pellet to which 900 µl of 2 mM $CaCl_2$/TBS was in turn added. The mixture was centrifuged again (2000 rpm, 5 min, 4° C.), and the resulting pellet was floated in 200 µl of 1 ml $CaCl_2$/TBS and used as a sample (G9 enzyme solution) for activity measurement. A portion of this was subjected to electrophoresis by SDS-PAGE and subsequently to western blotting with anti-FLAG M2 peroxidase (manufactured by Sigma) to confirm the expression of the G9 protein of interest. As a result, a band was detected at the position of approximately 45 kDa, and the expression was therefore confirmed.

After washing, the gel was supplemented with 30 µl of a buffer containing 50 mmol/l Tris-HCl (pH 7.4), 150 mmol/l NaCl, and 2 mmol/l EDTA and treated at 4° C. for 30 minutes to thereby elute the protein adsorbed in the gel. Then, the 10-minute centrifugation of the gel at 160×g yielded a supernatant. After the gel was supplemented again with 30 µl of a buffer containing 50 mmol/l Tris-HCl (pH 7.4), 150 mmol/l NaCl, and 2 mmol/l EDTA and treated at 4° C. for 10 minutes, the gel was centrifuged at 160×g for 10 minutes to thereby acquire a supernatant. Then, the above procedures were carried out again, and a total of 3 elution procedures were performed. The obtained eluate was supplemented with 1 mol/l $CaCl_2$ to be brought to 4 mmol/l at the final concentration. This eluate was used as an enzyme source.

Example 5

Analysis of G9 Enzyme Protein for Enzyme Activity (Activity Measurement using Glycolipid and Synthetic Monosaccharides, and so on, as Substrates)

The result of comparison with other glycosyltransferases known in the art on the basis of the amino acid sequence described in SEQ ID NO: 2 has suggested that the G9 is classified into transferases in light of, for example, the conservation of a sequence in the C-terminal region considered as an active site. Therefore, for example, UDP-GlcNAc can be used as a GlcNAc donor substrate to confirm the enzyme activity of the enzyme solution containing the G9 polypeptide, which has been obtained in Example 4 above.

In the present example, the activity of the G9 enzyme was measured according to almost the same method as methods described in the following references [1] to [3]:

[1] Shiraishi N, Natsume A, Togayachi A, Endo T, Akashima T, Yamada Y, Imai N, Nakagawa S, Koizumi S, Sekine S, Narimatsu H, Sasaki K., Identification and characterization of three novel beta 1,3-N-acetylglucosaminyltransferases structurally related to the beta 1,3-galactosyltransferase family., J Biol Chem., Feb. 2, 2001; 276(5): 3498-507.;

[2] Togayachi A, Akashima T, Ookubo R, Kudo T, Nishihara S, Iwasaki H, Natsume A, Mio H, Inokuchi J, Irimura T, Sasaki K, Narimatsu H., Molecular cloning and characterization of UDP-GlcNAc:lactosylceramide beta 1,3-N-acetylglucosaminyltransferase (beta 3Gn-T5), an essential enzyme for the expression of HNK-1 and Lewis X epitopes on glycolipids., J Biol chem., Jun. 22, 2001; 276(25): 22032-40.; and

[3] Iwai T, Inaba N, Naundorf A, Zhang Y, Gotoh M, Iwasaki H, Kudo T, Togayachi A, Ishizuka Y, Nakanishi H, Narimatsu H., Molecular cloning and characterization of a novel UDP-GlcNAc:GalNAc-peptide β 1,3-N acetylglucosaminyltransferase (β3Gn-T6), an enzyme synthesizing the core 3 structure of O-glycans., J Biol Chem., Jun. 22, 2001; 276(25): 22032-40.

(1) Investigation of Substrate Specificity

The FLAG peptide-fused G9 polypeptide obtained in the example above was measured for a β1,3-N-acetylglucosaminyltransferase activity with monosaccharaide/oligosaccharide/glycolipid/glycoprotein as substrates according to known methods (e.g., the above-described references and FEBS, 462, 289 (1999), J. Biol. Chem. 269, 14730-14737 (1994), J. Biol. Chem., 267, 23507 (1992), and J. Biol. Chem., 267, 2994 (1992)).

pNp-α-Glc, pNp-β-Glc, pNp-α-GlcNAc, pNp-β-GlcNAc, pNp-α-Gal, oNp-β-Gal, pNp-α-GalNAc, pNp-α-Xyl, oNp-β-Xyl, pNp-α-Fuc, Bz-α-Man, Bz-α-ManNAc, core1-α-pNp, core3-α-pNp, Bz-β-lactoside, GlcNAcβ1-4GlcNAcβ-Bz, and Galβ1-4GlcNAcα-pNp were used as acceptor substrates (see Table 5). These substrates can be purchased from, for example, Sigma Corp. or Toronto Research Chemicals Inc.

TABLE 5

Substrate specificity of G9

| | Acceptor substrate | Relative activity % |
|---|---|---|
| 1 | Galα-pNP[a] | ND |
| 2 | Galβ-oNP[a] | ND |
| 3 | GlcNAcα-Bz[b] | ND |
| 4 | GlcNAcβ-Bz[b] | ND |
| 5 | GalNAcα-pNP[a] | ND |
| 6 | GalNAcβ-pNP[b] | ND |
| 7 | Glcα-pNP[a] | ND |
| 8 | Glcβ-pNP[a] | ND |
| 9 | Fucα-pNP[a] | ND |
| 10 | Xylα-pNP[c] | ND |
| 11 | Xylβ-pNP[b] | ND |
| 12 | Manα-Bz[c] | ND |
| 13 | Lactoside β-Bz[b] | 27 |
| 14 | Galβ1-3GalNAcα-pNP (core 1)[c] | ND |
| 15 | GlcNAcβ1-3GalNAcα-pNP(core 2)[c] | ND |
| 16 | Galβ1-3GlcNAcβ-pNP[a] | ND |
| 17 | GlcNAcβ1-4GlcNAcβ-Bz[c] | ND |
| 18 | Galβ1-4GlcNAcα-pNP[c] | 100 |

(In Table 5, ND represents "not detected"; and the acceptor substrates marked by the superscript "a" were purchased from Calbiochem, the acceptor substrates marked by "b" were purchased from Sigma-Aldrich Corp, and the acceptor substrates marked by "c" were purchased from Toronto Research Chemicals Inc.)

A basic reaction solution in the case of using a radiolabeled substrate as the donor substrate comprises 20 µl in total of 14 mM HEPES buffer (pH 7.4), 10 mM $MnCl_2$, 0.15% Triton CF-54, 0.75 mM ATP, 50 µM UDP-GlcNAc (manufactured by Sigma), 4.5 μM (50 nCi) [$^{14}$C]UDP-GlcNAc (manufactured by Amersham Biosciences), 10 μM substrate (each of the above-described acceptor substrates), and an appropriate amount (5 to 10 μl) of the purified enzyme protein (enzyme source obtained in Example 4). Enzyme reaction was carried out at 37° C. for several hours up to 16 hours (usually for 16 hours).

After the completion of reaction, the resulting solution was supplemented with 200 μl of 0.1M KCl and lightly centrifuged, and then a supernatant was obtained. After being washed once with 10 ml of methanol, the supernatant was loaded onto Sep-Pak C18 Cartridge (Waters) equilibrated by two-time washing with 10 ml of 0.1 M KCl, and the substrate and a product in the supernatant were adsorbed in the cartridge. After the cartridge was washed twice with 1 ml of pure water for HPLC, the adsorbed substrate and product were eluted with 1 ml of methanol. Following the mixing with a liquid scintillator (ACSII; manufactured by Amersham Biosciences), the amount of radiation from the product was measured with a scintillation counter.

As a result, the G9 polypeptide exhibited the highest transferring activity for Galβ1-4GlcNAcα-pNp of the acceptor substrates tested and also exhibited a certain amount of transferring activity for Bz-β-lactoside (see Table 5).

(2) Investigation of Enzyme Reaction Conditions

Figure 2:
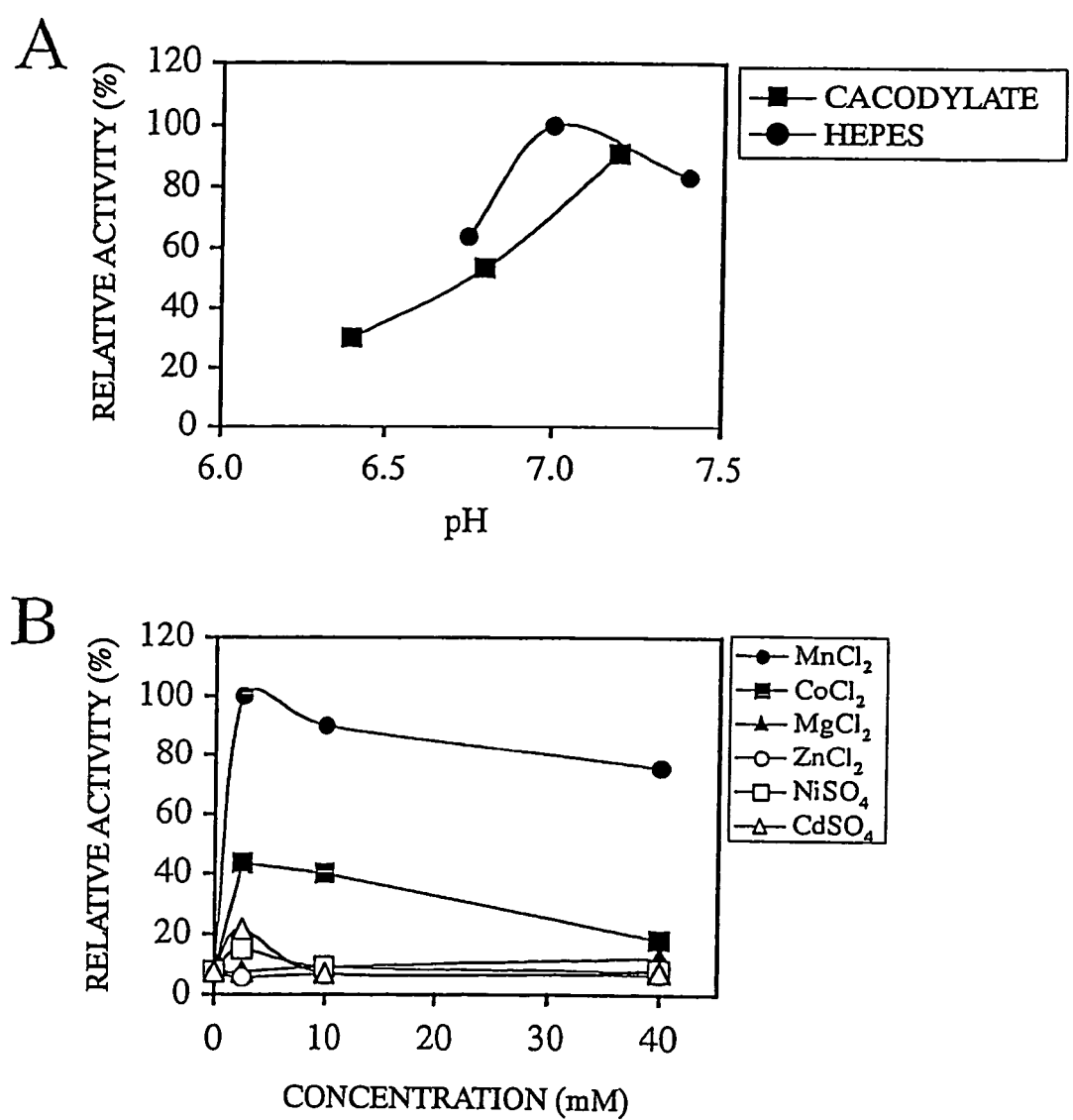
FIG. 2 shows a buffer in a reaction solution and pH dependence, and metal ion dependence, which are plotted for the activity of a G9 polypeptide.

Buffer conditions were investigated using the same reaction solution and reaction time as above but using HEPES (pH 6.75 to 7.4) and sodium cacodylate (pH 6.4 to 7.2) instead of 14 mM HEPES buffer (pH7.4) (see FIG. 2A).

As shown in FIG. 2A, the G9 polypeptide exhibited an activity in the case of using any of sodium cacodylate and HEPES. Generally, its activity was high at or around neutral. The G9 polypeptide had an activity that rises with an increase in pH within the neutral region from pH 6.4 to 7.2 in the sodium cacodylate and showed the maximum activity around pH 7.0 in the HEPES.

Since some glycosyltransferases require a metal ion, the metal ion requirement of the G9 enzyme was investigated. The same reaction solution and reaction time as above were used, and MnCl$_2$, CoCl$_2$, MgCl$_2$, ZnCl$_2$, NiCl$_2$, and CdCl$_2$ were used instead of 10 mM MnCl$_2$. The concentrations of each of the metal ions were set to 2.5, 10, and 40 mM, and the respective enzyme reactions were conducted (see FIG. 2B).

As shown in FIG. 2B, the activity of the G9 polypeptide is significantly enhanced in the presence of at least the Mn ion or Co ion of the divalent metal ions and particularly remarkably enhanced in the presence of the Mn ion. These enhanced activities rapidly rise in the low concentration region of the ion and subsequently gradually decrease. Although the Cd and Ni ions show slight enhancing effect in the low concentration region, no enhancing effect is substantially observed in the Mg and Zn ions.

The above results have demonstrated that the activity is shown most highly under the basic reaction conditions used in (1) above. The same conditions were used to carry out reaction in experiments below.

(3) Activity Measurement in the Case of using Oligosaccharides Pyridylaminated with 2-Aminopyridine (N-glycans) as Acceptor Substrates Commercially-available PA-oligosaccharides were used as substrates. An oligosaccharide can be pyridylaminated (PA) with 2-aminopyridine according to a standard method (Hase, S., Ibuki, T., and Ikenaka, T., J. Biochem. 95, 197-203 (1984)), and the PA-oligosaccharide was purchased from TAKARA SHUZO Co., Ltd. or SEIKAGAKU Corp. The specific test method is performed as follows:

After 16-hour reaction at 370° C. in a total of 20 μl of reaction solution containing 14 mM HEPES buffer (pH 7.4), 50 mM UDP-GlcNAc, 10 mM MnCl$_2$, 0.15% Triton CF-54, 40 pmol acceptor substrate (PA-oligosaccharide), and an appropriate amount (200 ng) of a purified enzyme protein, a product was detected by high performance liquid chromatography (HPLC; described below in detail). The enzyme purified with the anti-FLAG Ml antibody affinity gel in Example 4 was used as the above-described purified enzyme protein.

After the assay solution where the reaction was completed was treated at 100° C. for 5 minutes, the solution was supplemented with 8.0 μl of pure water for HPLC and centrifuged at 10,000×g for 5 minutes to obtain a supernatant. Subsequently, the supernatant was loaded onto an Ultrafree-MC column (manufactured by Millipore), and a portion (40 μl) thereof was subjected to HPLC. The Ultrafree-MC column was used according to the attached instruction.

HPLC was carried out using a PALPAK Type R column (TAKARA) as a column and Eluant A: 100 mM acetic acid/triethylamine (pH 4.0) and Eluant B: 100 mM acetic acid/triethylamine (pH 4.0)/0.5% 1-butanol as eluants under such conditions that: Eluant B gradient was 5 to 55% (0 to 60 minutes); a column temperature was 40° C.; and a flow rate was 1 ml/min. A product was detected using a fluorescence spectrum photometer RF-10AXL (manufactured by Shimadzu) (excitation wavelength at 320 nm and radiation wavelength at 400 nm).

As a result, the G9 polypeptide exhibited a significant activity for tetraantennary N-glycans (PA-004 and PA-011: Takara PA-substrate number) (see FIG. 3). By contrast, a β1,3-N-acetylglucosaminyltransferase 2 (β3GnT2) known in the art exhibits an activity for all types (PA-001 to –0011) of N-glycans, regardless of the number of an oligosaccharide. This also suggests that the G9 polypeptide in the present example has a selective activity, that is, it exhibits a significant activity for a tetraantennary N-glycan but exhibits no significant activity for monoantennary to triantennary N-glycans. In the result shown in FIG. 3, the activity of the G9 polypeptide appears relatively weak as compared to that of the β1,3-N-acetylglucosaminyltransferase 2. However, this is because the β1,3-N-acetylglucosaminyltransferase 2 is a homolog enzyme having a greatly strong enzyme activity.

(4) Activity Measurement in the Case of using Glycoproteins as Acceptor Substrates Enzyme reaction was carried out with glycoproteins as substrates. A reaction solution comprised 20 μl in total of 14 mM HEPES buffer (pH 7.4), 10 mM MnCl$_2$, 0.15% Triton CF-54, 0.75 mM ATP, 50 μM UDP-GlcNAc (manufactured by Sigma), 4.5 μM (50 nCi) [$^{14}$C]UDP-GlcNAc (manufactured by Amersham Biosciences), 40 μg of an acceptor substrate, and an appropriate amount (5 to 10 μl) of a purified enzyme protein. A α1-acid glycoprotein (orosomucoid; manufactured by Sigma), ovalbumin (manufactured by Sigma), or ovomucoid (manufactured by Sigma) was used as the above described acceptor substrate. The enzyme purified with the anti-FLAG M1 antibody affinity gel in Example 4 was used as the above-described purified enzyme protein.

Reaction was carried out at 37° C. for several hours up to 16 hours. A portion of a reaction product was subjected to enzyme digestion with glycopeptidase F (GPF; manufactured by TAKARA) according to the instruction. The samples both before and after enzyme digestion were analyzed by 10% SDS-PAGE (see FIG. 4).

As a result, the G9 polypeptide showed a GlcNAc-transferring activity for all of the glycoproteins (relatively weak activity for the ovalbumin) and the band disappeared by GPF digestion. This has demonstrated that such transferring reaction takes place against the N-glycan oligosaccharide of each glycoprotein.

Example 6

Construction of G9 Knockout Mouse

At least the ORF of an mG9 gene is likely to have a single exon. Created is a targeting vector (pBSK-mG9-KOneo) in which a chromosome fragment (approximately 10 kb) mainly having an approximately 10-kb fragment containing a region considered as the active domain of the mG9 desired to be knocked out (e.g., a nucleotide sequence from nucleotide No. 97 to 1194 in SEQ ID NO: 1) was inserted into pBluescript(R) II SK (−) (manufactured by TOYOBO). The pBSK-mG9-KOneo employs neo (neomycin-resistant gene) as a drug-resistant gene and lacks the predicted GlcNAc-transferring activity region of the mG9, and this lacking portion is replaced with the neo. After the pBSK-mG9-KOneo thus obtained is rendered linear with a restriction enzyme NotI, its 80-μg aliquot is transfected (e.g. electroporated) into ES cells (derived from an E14/129Sv mouse) to pick G418-resistant colonies. The G418-resistant colonies are transferred to a 24-well plate and cultured. After some of the cells are cryo-preserved, DNA is extracted from the remaining ES cells, and approximately 120 colonies of clones that have undergone recombination are selected by PCR. In addition, PCR and southern blotting, and so on, are used to ascertain that recombination occurs as planned. Ultimately, 10 clones of recombinants are selected. The ES cells from two of the selected clones are injected into the blastocyst of a C57BL/6 mouse. The murine embryo in which the ES cell has been injected is transplanted into the uterus of a foster mother mouse to generate a chimeric mouse. Then, a hetero-knockout mouse can be obtained by germ transmission.

The invention claimed is:

1. An isolated β1,3-N-acetyl-D-glucosaminyltransferase protein comprising the amino acid sequence of SEQ ID NO: 2 or SEQ ID NO: 16.

2. The protein of claim 1 comprising the amino acid sequence of SEQ ID NO: 2.

3. The protein of claim 1 comprising the amino acid sequence of SEQ ID NO: 16.

4. A method for transferring N-acetyl-D-glucosamine from a donor substrate to an acceptor substrate through β1,3-linkage, the method comprising reacting the donor substrate and the acceptor substrate in the presence of a β1,3-N-acetyl-D-glucosaminyltransferase protein, wherein the protein comprises the amino acid sequence of SEQ ID NO: 2 or SEQ ID NO: 16.

5. The method according to claim 4, wherein the protein comprises the amino acid sequence of SEQ ID NO: 2.

6. The method according to claim 4, wherein the protein comprises the amino acid sequence of SEQ ID NO: 16.

* * * * *

SEQUENCE LISTING

<160> NUMBER OF SEQ ID NOS: 20

<210> SEQ ID NO 1
<211> LENGTH: 1194
<212> TYPE: DNA
<213> ORGANISM: Homo sapiens

<400> SEQUENCE: 1

```
atgcgctgcc ccaagtgcct tctctgcctg tcagcactgc tcacactcct gggcctcaaa      60
gtgtacatcg agtggacatc cgagtcccgg ctcagcaagg cctaccccag ccctcggggc     120
accccgccaa gccccacgcc agccaaccct gagcccaccc tacctgccaa cctctccacc     180
cgcctgggcc agactatccc gctgccctt gcttactgga accagcagca gtggcggctg      240
gggtccctgc ccagtgggga cagcactgaa acgggggct gccaggcttg ggggggccgcc    300 gccgccaccg agatccctga cttcgcctcc taccccaagg acctccgccg cttcttgctg     360
tcagcagcct gccggagctt cccacagtgg ctgcctggag gtggtggcag ccaagtctcc     420
agctgctcag atactgatgt cccctacctg ctgttggccg tcaagtcaga accagggcgc     480
tttgcagaac gacaggccgt gagagagacg tggggcagtc cagctccagg gatccggctg     540
ctcttcctgc tagggtctcc ggtgggtgag gcggggcctg acctagactc actagtggcc     600
tgggagagcc gtcgctacag tgacctgctg ctctgggact tcctcgacgt cccattcaac     660
cagacgctca aagacctgct gctgctggcc tggctgggcc gccactgccc caccgtgagt     720
tttgtcttgc gagctcagga cgatgccttt gtacacaccc ctgccctgct ggctcacctg     780
cgggccctgc cacctgcctc ggcccgaagc ctctacctgg gtgaggtctt tacccaggcc     840
atgcctctcc ggaagccagg aggacccttc tatgtgcccg agtccttctt cgaaggtggc     900
tacccagcct atgcaagcgg gggtggctac gtcattgccg ggcgcctggc accctggctg     960
ctgcgggcgg cagcccgtgt ggcacccttc cccttgagg acgtctacac tggcctttgc    1020
atccgagccc tgggcctggt gccccaggcc cacccaggct tcctcacagc ctggccagca    1080
gaccgcactg cggaccactg tgctttccgc aacctgctgc tggtacggcc cctgggcccc    1140
caggccagca ttcggctctg gaaacaactg caagacccaa ggctccagtg ctga         1194
```

<210> SEQ ID NO 2
<211> LENGTH: 397

```
<212> TYPE: PRT
<213> ORGANISM: Homo sapiens

<400> SEQUENCE: 2

Met Arg Cys Pro Lys Cys Leu Leu Cys Leu Ser Ala Leu Leu Thr Leu
1               5                   10                  15

Leu Gly Leu Lys Val Tyr Ile Glu Trp Thr Ser Glu Ser Arg Leu Ser
            20                  25                  30

Lys Ala Tyr Pro Ser Pro Arg Gly Thr Pro Ser Pro Thr Pro Ala
        35                  40                  45

Asn Pro Glu Pro Thr Leu Pro Ala Asn Leu Ser Thr Arg Leu Gly Gln
    50                  55                  60

Thr Ile Pro Leu Pro Phe Ala Tyr Trp Asn Gln Gln Trp Arg Leu
65                  70                  75                  80

Gly Ser Leu Pro Ser Gly Asp Ser Thr Glu Thr Gly Gly Cys Gln Ala
                85                  90                  95

Trp Gly Ala Ala Ala Thr Glu Ile Pro Asp Phe Ala Ser Tyr Pro
            100                 105                 110

Lys Asp Leu Arg Arg Phe Leu Leu Ser Ala Ala Cys Arg Ser Phe Pro
            115                 120                 125

Gln Trp Leu Pro Gly Gly Gly Ser Gln Val Ser Ser Cys Ser Asp
130                 135                 140

Thr Asp Val Pro Tyr Leu Leu Leu Ala Val Lys Ser Glu Pro Gly Arg
145                 150                 155                 160

Phe Ala Glu Arg Gln Ala Val Arg Glu Thr Trp Gly Ser Pro Ala Pro
                165                 170                 175

Gly Ile Arg Leu Leu Phe Leu Leu Gly Ser Pro Val Gly Glu Ala Gly
            180                 185                 190

Pro Asp Leu Asp Ser Leu Val Ala Trp Glu Ser Arg Arg Tyr Ser Asp
        195                 200                 205

Leu Leu Leu Trp Asp Phe Leu Asp Val Pro Phe Asn Gln Thr Leu Lys
            210                 215                 220

Asp Leu Leu Leu Ala Trp Leu Gly Arg His Cys Pro Thr Val Ser
225                 230                 235                 240

Phe Val Leu Arg Ala Gln Asp Asp Ala Phe Val His Thr Pro Ala Leu
                245                 250                 255

Leu Ala His Leu Arg Ala Leu Pro Pro Ala Ser Ala Arg Ser Leu Tyr
            260                 265                 270

Leu Gly Glu Val Phe Thr Gln Ala Met Pro Leu Arg Lys Pro Gly Gly
        275                 280                 285

Pro Phe Tyr Val Pro Glu Ser Phe Glu Gly Gly Tyr Pro Ala Tyr
290                 295                 300

Ala Ser Gly Gly Gly Tyr Val Ile Ala Gly Arg Leu Ala Pro Trp Leu
305                 310                 315                 320

Leu Arg Ala Ala Ala Arg Val Ala Pro Phe Pro Phe Glu Asp Val Tyr
                325                 330                 335

Thr Gly Leu Cys Ile Arg Ala Leu Gly Leu Val Pro Gln Ala His Pro
            340                 345                 350

Gly Phe Leu Thr Ala Trp Pro Ala Asp Arg Thr Ala Asp His Cys Ala
        355                 360                 365

Phe Arg Asn Leu Leu Leu Val Arg Pro Leu Gly Pro Gln Ala Ser Ile
    370                 375                 380

Arg Leu Trp Lys Gln Leu Gln Asp Pro Arg Leu Gln Cys
385                 390                 395     397
```

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: 5' primer
      for PCR

<400> SEQUENCE: 3
ctcaagctta tgcgctgccc caagtgcctt c                                    31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: 3' primer
      for PCR

<400> SEQUENCE: 4
ctcgaattct cagcactgga gccttgggtc t                                    31

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: 5' primer
      for RT-PCR

<400> SEQUENCE: 5
gctgttggcc gtcaagtcag                                                 20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: 3' primer
      for RT-PCR

<400> SEQUENCE: 6
caggaagagc agccggat                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: probe for
      RT-PCR

<400> SEQUENCE: 7
cagaacgaca ggccgtga                                                   18

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: 5' primer
      for PCR

<400> SEQUENCE: 8
gccaagctta catccgagtc ccggctcag                                       29

```
<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: 5' primer
      for PCR

<400> SEQUENCE: 9
gccaagctta aggcctaccc cagccctcg                                      29

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: 3' primer
      for PCR

<400> SEQUENCE: 10
cggaattctc agcactggag ccttgggt                                       28

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: 5' primer
      for PCR

<400> SEQUENCE: 11
ggggacaagt ttgtacaaaa aagcaggctt ccccagccct cggggcaccc cgcca         55

<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence: 3' primer
      for PCR

<400> SEQUENCE: 12
ggggaccact ttgtacaaga aagctgggtc tcagcactgg agccttgggt cttg          54

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: 5' primer
      for PCR

<400> SEQUENCE: 13
gccaagctta catccgagtc ccggctcag                                      29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: 5' primer
      for PCR

<400> SEQUENCE: 14
gccaagctta aggcctaccc cagccctcg                                      29
```

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: 3' primer for PCR

<400> SEQUENCE: 15
cggaattctc agcactggag ccttgggt                                           28

<210> SEQ ID NO 16
<211> LENGTH: 372
<212> TYPE: PRT
<213> ORGANISM: Homo sapiens

<400> SEQUENCE: 16

```
Thr Ser Glu Ser Arg Leu Ser Lys Ala Tyr Pro Ser Pro Arg Gly Thr
1               5                  10                  15

Pro Pro Ser Pro Thr Pro Ala Asn Pro Glu Pro Thr Leu Pro Ala Asn
            20                  25                  30

Leu Ser Thr Arg Leu Gly Gln Thr Ile Pro Leu Pro Phe Ala Tyr Trp
        35                  40                  45

Asn Gln Gln Trp Arg Leu Gly Ser Leu Pro Ser Gly Asp Ser Thr
    50                  55                  60

Glu Thr Gly Gly Cys Gln Ala Trp Gly Ala Ala Ala Thr Glu Ile
65              70                  75                  80

Pro Asp Phe Ala Ser Tyr Pro Lys Asp Leu Arg Arg Phe Leu Leu Ser
                85                  90                  95

Ala Ala Cys Arg Ser Phe Pro Gln Trp Leu Pro Gly Gly Gly Ser
            100                 105                 110

Gln Val Ser Ser Cys Ser Asp Thr Asp Val Pro Tyr Leu Leu Leu Ala
        115                 120                 125

Val Lys Ser Glu Pro Gly Arg Phe Ala Glu Arg Gln Ala Val Arg Glu
    130                 135                 140

Thr Trp Gly Ser Pro Ala Pro Gly Ile Arg Leu Leu Phe Leu Leu Gly
145                 150                 155                 160

Ser Pro Val Gly Glu Ala Gly Pro Asp Leu Asp Ser Leu Val Ala Trp
                165                 170                 175

Glu Ser Arg Arg Tyr Ser Asp Leu Leu Leu Trp Asp Phe Leu Asp Val
            180                 185                 190

Pro Phe Asn Gln Thr Leu Lys Asp Leu Leu Leu Ala Trp Leu Gly
        195                 200                 205

Arg His Cys Pro Thr Val Ser Phe Val Leu Arg Ala Gln Asp Asp Ala
    210                 215                 220

Phe Val His Thr Pro Ala Leu Leu Ala His Leu Arg Ala Leu Pro Pro
225                 230                 235                 240

Ala Ser Ala Arg Ser Leu Tyr Leu Gly Glu Val Phe Thr Gln Ala Met
                245                 250                 255

Pro Leu Arg Lys Pro Gly Gly Pro Phe Tyr Val Pro Glu Ser Phe Phe
            260                 265                 270

Glu Gly Gly Tyr Pro Ala Tyr Ala Ser Gly Gly Tyr Val Ile Ala
        275                 280                 285

Gly Arg Leu Ala Pro Trp Leu Leu Arg Ala Ala Arg Val Ala Pro
    290                 295                 300

Phe Pro Phe Glu Asp Val Tyr Thr Gly Leu Cys Ile Arg Ala Leu Gly
305                 310                 315                 320
```

```
Leu Val Pro Gln Ala His Pro Gly Phe Leu Thr Ala Trp Pro Ala Asp
            325                 330                 335

Arg Thr Ala Asp His Cys Ala Phe Arg Asn Leu Leu Val Arg Pro
            340                 345                 350

Leu Gly Pro Gln Ala Ser Ile Arg Leu Trp Lys Gln Leu Gln Asp Pro
            355                 360                 365

Arg Leu Gln Cys
        370     372

<210> SEQ ID NO 17
<211> LENGTH: 282
<212> TYPE: PRT
<213> ORGANISM: Homo sapiens

<400> SEQUENCE: 17

Arg Arg Phe Leu Leu Ser Ala Ala Cys Arg Ser Phe Pro Gln Trp Leu
1               5                   10                  15

Pro Gly Gly Gly Gly Ser Gln Val Ser Ser Cys Ser Asp Thr Asp Val
            20                  25                  30

Pro Tyr Leu Leu Leu Ala Val Lys Ser Glu Pro Gly Arg Phe Ala Glu
            35                  40                  45

Arg Gln Ala Val Arg Glu Thr Trp Gly Ser Pro Ala Pro Gly Ile Arg
        50                  55                  60

Leu Leu Phe Leu Leu Gly Ser Pro Val Gly Glu Ala Gly Pro Asp Leu
65                  70                  75                  80

Asp Ser Leu Val Ala Trp Glu Ser Arg Arg Tyr Ser Asp Leu Leu Leu
                85                  90                  95

Trp Asp Phe Leu Asp Val Pro Phe Asn Gln Thr Leu Lys Asp Leu Leu
            100                 105                 110

Leu Leu Ala Trp Leu Gly Arg His Cys Pro Thr Val Ser Phe Val Leu
        115                 120                 125

Arg Ala Gln Asp Asp Ala Phe Val His Thr Pro Ala Leu Leu Ala His
130                 135                 140

Leu Arg Ala Leu Pro Pro Ala Ser Ala Arg Ser Leu Tyr Leu Gly Glu
145                 150                 155                 160

Val Phe Thr Gln Ala Met Pro Leu Arg Lys Pro Gly Gly Pro Phe Tyr
                165                 170                 175

Val Pro Glu Ser Phe Phe Glu Gly Gly Tyr Pro Ala Tyr Ala Ser Gly
            180                 185                 190

Gly Gly Tyr Val Ile Ala Gly Arg Leu Ala Pro Trp Leu Leu Arg Ala
        195                 200                 205

Ala Ala Arg Val Ala Pro Phe Pro Phe Glu Asp Val Tyr Thr Gly Leu
    210                 215                 220

Cys Ile Arg Ala Leu Gly Leu Val Pro Gln Ala His Pro Gly Phe Leu
225                 230                 235                 240

Thr Ala Trp Pro Ala Asp Arg Thr Ala Asp His Cys Ala Phe Arg Asn
                245                 250                 255

Leu Leu Leu Val Arg Pro Leu Gly Pro Gln Ala Ser Ile Arg Leu Trp
            260                 265                 270

Lys Gln Leu Gln Asp Pro Arg Leu Gln Cys
        275                 280     282

<210> SEQ ID NO 18
<211> LENGTH: 1845
<212> TYPE: DNA
```

<213> ORGANISM: Mouse

<400> SEQUENCE: 18

| | | | | | |
|---|---|---|---|---|---|
| ggaggacgca | cagctgcgag | gagggagtcc | gggcagggct | ttacccgagg | acccccagag | 60 |
| ctggcggaag | ctggacccag | aggtacctgg | ggccccaggc | cctggggtgg | ggttactgga | 120 |
| ggaggtaggt | aggcttccaa | gaaggtaaaa | aggagtttcc | ccgggaagct | gggactcctg | 180 |
| aagagacaga | ggaatgaggg | aagggagta | ggaagagccg | ttggagcgat | actgcaaata | 240 |
| gatataacac | catgactgca | gaaaaggaaa | gaatgggggg | tcgaggggag | gcggtgttca | 300 |
| gtctaggata | acgttaagtt | gggtactgta | gttcagtctg | cctagggtca | gagtctcaga | 360 |
| agccattaac | agaactgggt | aggacctagg | ctgcttgcct | gggcttcgct | gggccgtctt | 420 |
| tggagatcca | ccctgcaccc | taaagacttc | tgtggctcct | tgtgactctt | gcagccccac | 480 |
| tggtggccct | ttccctgggc | cgggtcatgc | gttgccgcaa | gtgccagctc | tgcctgtcag | 540 |
| cactgctcac | actcctgggc | ctcaaagtat | acatcgagtg | gacatccgag | tcctggctta | 600 |
| aaaaggctga | accccggggc | gctctgccca | gtcccacacc | acccaatgct | gagcccactc | 660 |
| tgcccaccaa | cctctcagca | cgcctgggtc | agactggccc | actgtcctct | gcttactgga | 720 |
| accagcagca | gcggcagctg | ggagtcctgc | ccagtacgga | ctgtcagact | gggggactg | 780 |
| ttgctgcctc | ggagatcttg | gacttcatcc | tgtaccccca | ggagcttcgg | cgcttcttgc | 840 |
| tgtcggcggc | ctgtaggagc | tttccactat | ggctgcctgc | aggagaaggc | agccctgtgg | 900 |
| ccagctgctc | tgataaggat | gtaccctact | tgctactggc | tgtcaaatca | gaaccaggac | 960 |
| actttgcagc | acggcaggct | gtgagggaga | cctggggcag | cccagttgct | gggacccggt | 1020 |
| tgctcttcct | gctggggtcc | ccctaggaa | tgggggggcc | tgacttaaga | tcactggtga | 1080 |
| cgtgggaaag | ccggcgctat | ggtgacctac | tgctctggga | cttcctggat | gttccctaca | 1140 |
| accggacact | caaggacctg | ctgctgctga | cctggctgag | ccaccactgc | ccgatgtca | 1200 |
| attttgtcct | gcaggttcag | gatgatgcct | tgtgcacat | cccagccta | ctggagcacc | 1260 |
| tgcagactct | gccacccacc | tgggcccgca | gcctctacct | gggtgagatc | ttcacccagg | 1320 |
| ccaaaccgct | ccgcaagccc | ggaggaccct | tctatgtgcc | gaagaccttc | tttgaagggg | 1380 |
| actatccagc | ctatgcgagt | ggaggtggct | atgtaatctc | aggacgcctg | gcaccctggc | 1440 |
| tgctgcaggc | ggcagctcgc | gtggcaccct | tccccttga | tgatgtctac | actggcttct | 1500 |
| gcttccgtgc | cctgggctta | gcaccccgtg | cccatccagg | cttcctcaca | gcctggccag | 1560 |
| cagaacgtac | cagggacccc | tgcgccgtgc | gaggcctgct | cttggtgcat | ccagtcagcc | 1620 |
| ctcaggacac | catttggctc | tggagacatc | tgtgggtccc | agagctccag | tgctgaccgg | 1680 |
| cagagacaag | ctggggtggg | tgggtgctga | cctggcctga | gtctctccta | gagacaagct | 1740 |
| ggggtgggtg | gggctgacct | ggcctgagtc | tctcctaaac | ccttcttagc | caaggtggca | 1800 |
| gactgtgttt | atctacttta | tggttttgaa | aaatgtgtcc | ttcct | | 1845 |

<210> SEQ ID NO 19
<211> LENGTH: 1170
<212> TYPE: DNA
<213> ORGANISM: Mouse

<400> SEQUENCE: 19

| | | | | | |
|---|---|---|---|---|---|
| atgcgttgcc | gcaagtgcca | gctctgcctg | tcagcactgc | tcacactcct | gggcctcaaa | 60 |
| gtatacatcg | agtggacatc | cgagtcctgg | cttaaaaagg | ctgaaccccg | gggcgctctg | 120 |
| cccagtccca | caccacccaa | tgctgagccc | actctgccca | ccaacctctc | agcacgcctg | 180 |

-continued

```
ggtcagactg gcccactgtc ctctgcttac tggaaccagc agcagcggca gctgggagtc      240
ctgcccagta cggactgtca gacttggggg actgttgctg cctcggagat cttggacttc      300
atcctgtacc cccaggagct tcggcgcttc ttgctgtcgg cggcctgtag gagctttcca      360
ctatggctgc ctgcaggaga aggcagccct gtggccagct gctctgataa ggatgtaccc      420
tacttgctac tggctgtcaa atcagaacca ggacactttg cagcacggca ggctgtgagg      480
gagacctggg gcagccagt tgctgggacc cggttgctct tcctgctggg gtcccccta       540 ggaatggggg ggcctgactt aagatcactg gtgacgtggg aaagccggcg ctatggtgac      600
ctactgctct gggacttcct ggatgttccc tacaaccgga cactcaagga cctgctgctg      660
ctgacctggc tgagccacca ctgccccgat gtcaattttg tcctgcaggt tcaggatgat      720
gcctttgtgc acatcccagc cctactggag cacctgcaga ctctgccacc cacctgggcc      780
cgcagcctct acctgggtga gatcttcacc caggccaaac cgctccgcaa gcccggagga      840
cccttctatg tgccgaagac cttctttgaa ggggactatc agcctatgc gagtggaggt       900 ggctatgtaa tctcaggacg cctggcaccc tggctgctgc aggcggcagc tcgcgtggca      960
cccttcccct tgatgatgt ctacactggc ttctgcttcc gtgccctggg cttagcaccc      1020
cgtgcccatc caggcttcct cacagccctgg ccagcagaac gtaccaggga cccctgcgcc     1080
gtgcgaggcc tgctcttggt gcatccagtc agccctcagg acaccatttg gctctggaga     1140
catctgtggg tcccagagct ccagtgctga                                       1170
```

<210> SEQ ID NO 20
<211> LENGTH: 389
<212> TYPE: PRT
<213> ORGANISM: Mouse

<400> SEQUENCE: 20

```
Met Arg Cys Arg Lys Cys Gln Leu Cys Leu Ser Ala Leu Leu Thr Leu
1               5                   10                  15

Leu Gly Leu Lys Val Tyr Ile Glu Trp Thr Ser Glu Ser Trp Leu Lys
            20                  25                  30

Lys Ala Glu Pro Arg Gly Ala Leu Pro Ser Pro Thr Pro Pro Asn Ala
        35                  40                  45

Glu Pro Thr Leu Pro Thr Asn Leu Ser Ala Arg Leu Gly Gln Thr Gly
    50                  55                  60

Pro Leu Ser Ser Ala Tyr Trp Asn Gln Gln Arg Gln Leu Gly Val
65                  70                  75                  80

Leu Pro Ser Thr Asp Cys Gln Thr Trp Gly Thr Val Ala Ala Ser Glu
                85                  90                  95

Ile Leu Asp Phe Ile Leu Tyr Pro Gln Glu Leu Arg Arg Phe Leu Leu
            100                 105                 110

Ser Ala Ala Cys Arg Ser Phe Pro Leu Trp Leu Pro Ala Gly Glu Gly
        115                 120                 125

Ser Pro Val Ala Ser Cys Ser Asp Lys Asp Val Pro Tyr Leu Leu Leu
    130                 135                 140

Ala Val Lys Ser Glu Pro Gly His Phe Ala Ala Arg Gln Ala Val Arg
145                 150                 155                 160

Glu Thr Trp Gly Ser Pro Val Ala Gly Thr Arg Leu Leu Phe Leu Leu
                165                 170                 175

Gly Ser Pro Leu Gly Met Gly Gly Pro Asp Leu Arg Ser Leu Val Thr
            180                 185                 190
```

```
                            -continued
Trp Glu Ser Arg Arg Tyr Gly Asp Leu Leu Leu Trp Asp Phe Leu Asp
        195                 200                 205

Val Pro Tyr Asn Arg Thr Leu Lys Asp Leu Leu Leu Leu Thr Trp Leu
        210                 215                 220

Ser His His Cys Pro Asp Val Asn Phe Val Leu Gln Val Gln Asp Asp
225                 230                 235                 240

Ala Phe Val His Ile Pro Ala Leu Leu Glu His Leu Gln Thr Leu Pro
                245                 250                 255

Pro Thr Trp Ala Arg Ser Leu Tyr Leu Gly Glu Ile Phe Thr Gln Ala
                260                 265                 270

Lys Pro Leu Arg Lys Pro Gly Gly Pro Phe Tyr Val Pro Lys Thr Phe
        275                 280                 285

Phe Glu Gly Asp Tyr Pro Ala Tyr Ala Ser Gly Gly Gly Tyr Val Ile
        290                 295                 300

Ser Gly Arg Leu Ala Pro Trp Leu Leu Gln Ala Ala Ala Arg Val Ala
305                 310                 315                 320

Pro Phe Pro Phe Asp Asp Val Tyr Thr Gly Phe Cys Phe Arg Ala Leu
                325                 330                 335

Gly Leu Ala Pro Arg Ala His Pro Gly Phe Leu Thr Ala Trp Pro Ala
                340                 345                 350

Glu Arg Thr Arg Asp Pro Cys Ala Val Arg Gly Leu Leu Leu Val His
            355                 360                 365

Pro Val Ser Pro Gln Asp Thr Ile Trp Leu Trp Arg His Leu Trp Val
        370                 375                 380

Pro Glu Leu Gln Cys
385             389
```